(12) United States Patent
Lindsay

(10) Patent No.: US 6,468,473 B1
(45) Date of Patent: *Oct. 22, 2002

(54) SELF-CONTAINED PACK ASSEMBLY FOR AN EXTRACORPOREAL BLOOD CIRCUIT

(75) Inventor: Erin Jessica Lindsay, Manchester, MI (US)

(73) Assignee: Terumo Cardiovascular Systems Corporation, Somerset, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 09/466,933

(22) Filed: Dec. 20, 1999

Related U.S. Application Data

(63) Continuation-in-part of application No. 09/244,426, filed on Feb. 10, 1999, now Pat. No. 6,306,346.

(51) Int. Cl.[7] .......................... A61M 1/14; A61M 37/00; A61M 1/36
(52) U.S. Cl. ....................... 422/45; 604/4.01; 604/6.14; 604/6.15; 261/DIG. 28
(58) Field of Search ................................ 604/4.01, 5.01, 604/6.01, 6.13–6.14; 422/44–48; 600/19; 261/DIG. 28; 333/202; 60/325

(56) References Cited

U.S. PATENT DOCUMENTS

| | | |
|---|---|---|
| 4,083,777 A | 4/1978 | Hutchisson |
| 4,149,635 A | 4/1979 | Stevens |
| 4,370,983 A | 2/1983 | Lichtenstein |
| 4,420,085 A | 12/1983 | Wilson et al. |
| 4,436,620 A | 3/1984 | Bellotti et al. |
| 4,479,761 A | 10/1984 | Bilstad et al. |
| 4,479,762 A | 10/1984 | Bilstad et al. |
| 4,765,959 A * | 8/1988 | Fukasawa .............. 210/321.78 |
| 4,850,954 A | 7/1989 | Charvin |
| 5,266,265 A | 11/1993 | Raible |
| 5,476,444 A | 12/1995 | Keeling et al. |
| 5,540,653 A | 7/1996 | Schock et al. |
| 5,643,190 A | 7/1997 | Utterberg |
| 5,750,025 A | 5/1998 | Holmes et al. |
| 5,753,173 A | 5/1998 | Leonard et al. |
| 5,800,721 A * | 9/1998 | McBride ..................... 210/188 |
| 5,823,986 A | 10/1998 | Peterson |
| 5,957,879 A | 9/1999 | Roberts et al. |
| 5,958,338 A * | 9/1999 | Lindsay et al. ............... 422/45 |
| 6,306,346 B1 * | 10/2001 | Lindsay ............... 261/DIG. 28 |

OTHER PUBLICATIONS

Lonsky, et al., "How Long Can the Previously Assembled Cardiopulmonary Bypass Circuit Stay Sterile?", ACTA MEDCIA, vol. 41, pp 91–93 (1998).

Cobe Blue Ribbon Packs, "The World's Recognized Leader in Fully Integrated, Pre–Connected Bypass Circuits," p. 1–2, http:/www,cobecv.com/bluribbn.html.

Amsect Today, Jan. 1998, advertisement, "Fast Start. Smooth Finish. Introducing The Medtronic MicroCircuit, " © 1997 Medtronic, Inc.

Cobe Blue Ribbon Pack, advertisement, "There's more to this package than meets the eye," Cobe Cardiovascular.

Cobe Blue Ribbon Pack, advertisement, "With Cobe® Blue Ribbon Pack® Heart–Lung Circuits, there's much less hand movement, " Cobe Cardiovascular.

* cited by examiner

*Primary Examiner*—Angela D. Sykes
*Assistant Examiner*—P. M. Bianco
(74) *Attorney, Agent, or Firm*—Burns, Doane, Swecker & Mathis, LLP

(57) ABSTRACT

A self-contained pack assembly includes all of the disposable components of an extracorporeal support circuit for cardiac bypass surgery. The pack assembly comprises a blood reservoir, a blood oxygenator, and a carrier for mounting the blood reservoir and blood oxygenator. One or more trays may be releasably attached to the carrier to serve as storage containers for coiled tubing used in the support circuit. Pre-made connections can also be formed between the tubing and the blood reservoir and blood and oxygenator as may be desired.

25 Claims, 20 Drawing Sheets

SELF-CONTAINED PACK ASSEMBLY FOR AN EXTRACORPOREAL BLOOD CIRCUIT

CROSS-REFERENCE TO RELATED APPLICATION

This application is a continuation-in-part of pending application U.S. Ser. No. 09/244,426, filed Feb. 10, 1999, now U.S. Pat. No. 6,306,346 B1, the entire contents of which are hereby incorporated by reference.

TECHNICAL FIELD

The present invention relates to extracorporeal blood circuits for oxygenation and circulation of a patient's blood during cardiac bypass surgery or similar procedures, and in particular to a self-contained pack assembly that includes the tubing and other disposable components of an extracorporeal blood circuit.

BACKGROUND OF THE INVENTION

During cardiac bypass surgery a patient's heart is slowed or stopped for surgical repair, and his or her blood must be artificially oxygenated and pumped through the body using an extracorporeal support circuit. Using this system, venous blood is diverted from entering the right chambers of the heart and is instead directed through a series of tubes, pumps and filters, which provide fresh oxygen to the blood and return it to the body's systemic circulation at the aorta. The oxygenated blood is then circulated throughout the body. The circuit thus ensures that the patient continues to be nourished by oxygenated blood flow while the heart is unable to function.

In performing such a procedure, a complicated multi-component system is required. One or two blood reservoirs, an oxygenator (possibly combined with a heat exchanger), a blood pump, and multiple tubes to connect the various components are needed and must be assembled and arranged before surgery may begin. Typically a significant amount of time must be spent just prior to surgery to accomplish the set-up, and great attention must be paid to the details of this complicated task.

In a conventional extracorporeal support circuit, a venous line drains blood from the right side of the patient's heart and delivers it to a blood reservoir. The blood is then pumped by a specially designed pump from the outlet of the blood reservoir into a blood oxygenator for oxygenation and cooling. The oxygenated blood is artificially pumped via an arterial line to the venous line, and the circuit is continued in this fashion until the surgical repair is complete.

The support circuit normally includes a blood scavenging sub-circuit for recovering and recycling blood from the surgical field. The sub-circuit includes one or more suckers (typically two to four) for sucking blood from the surgical field. Vacuum is applied to the suckers by a peristaltic positive displacement pump (also known as a roller pump) or wall vacuum to deliver the scavenged blood to a cardiotomy reservoir. The cardiotomy reservoir includes a defoaming section to remove entrained air and a filter. The outlet for the cardiotomy reservoir delivers the de-foamed, filtered blood to the venous blood reservoir of the main circuit. Various cardiotomy reservoirs are described in U.S. Pat. Nos. 3,891,416, 3,993,461, 4,208,193 and 4,243,531. The cardiotomy reservoir may alternatively be an integral portion of the venous blood reservoir in which the scavenged blood flows through a filter section and the venous blood does not.

A schematic diagram of a conventional "open" extracorporeal support system is shown in FIG. 1. A hardshell reservoir 20 is provided for cleaning, debubbling, and collecting the blood. This type of system is called an "open" system because the hardshell reservoir 20 is vented, and thus open to the atmosphere. A tubing assembly called a pump loop 22 includes a pump inlet line 24 and a pump outlet line 26. These two lines are connected to an arterial pump 28, which for the purposes of this invention will most conveniently be of the type which has a pump header 30 which is separable from the motor portion. The pump outlet 26 leads to the inlet of the oxygenator 32, which may include a heat exchanger 34.

The elements so far described are connected to the body of the patient by a tubing assembly called an A-V loop 36. The A-V loop 36 includes a venous line 38 to carry the patient's low-pressure, oxygen depleted venous blood to the reservoir, and an arterial line 40 carrying high-pressure, oxygen rich arterial blood from the oxygenator 32 back to the patient. It may be convenient to monitor the condition of the blood in these two lines, so a blood parameter monitor 42 may be provided having sensors 44 and 46, which are kept in chemical equilibrium with the blood flowing in the venous line 38 and the arterial line 40, respectively. A hematocrit monitor 48 may also be provided, having its own sensor 50, conveniently monitoring the blood in the venous line 38.

It may be convenient to perfuse the patient's heart directly with a different solution than is provided to the rest of the patient's body. Cardioplegia solution is typically used in this fashion to slow or stop the patient's heart during surgery. A cardioplegia pump 52 may be used to deliver cardioplegia solution supplied by solution line 56 from a solution supply 58. The cardioplegia pump outlet line 60 passes through a cardioplegia heat exchanger 62 and a bubble trap 64 before delivering cardioplegia solution to the heart at the cardioplegia catheter 66.

Two suction lines are typically provided to recapture blood from the site of the surgical incision that has escaped the closed system. The first is called the vent line 68, and runs from a vent catheter 70 through a vent pump 72 to the reservoir 20. The second is called the suction line 74, and runs from a suction device 76 through a suction pump 78 and once again to the reservoir 20.

A further embodiment of the prior art system utilizes a flexible venous reservoir. A system having a flexible venous reservoir utilizes gravity to drain the cardiotomy blood to the venous reservoir, since the flexible venous reservoir is not vented. Such a system is called a "closed" system because there is minimal blood-air contact.

To prepare the above-described systems for use, each of the tubing connections must be individually made by a skilled person in the operating room. Many of these connections are between disposable system components, such as tubes and filters, which could advantageously be pre-connected and assembled in an assembly pack for quick attachment to the nondisposable elements of the system, thus enhancing operating room efficiency. Furthermore, because the operating room protocol differs between hospitals, the assembly pack should be capable of accommodating either a closed system or an open system, as described above, depending upon the particular procedures followed by a hospital. However, no such assembly packs have heretofore been developed in the art.

SUMMARY OF THE INVENTION

The present invention provides an assembly pack that contains the major disposable components of an extracorporeal support circuit, conveniently packaged in ready-to-use condition. All the tubing needed to connect the patient for bypass surgery is included in the pack, with all or some of the necessary attachments between the various elements in the pack being optionally pre-made in a sterilized condition. In preparation for surgery, when the attachments are pre-made, only a few connections must be made between the assembly pack and the nondisposable elements of the circuit compared to the numerous connections that were previously required. The assembly pack allows one to carry and mount all of the disposable paraphernalia needed for perfusion with a single hand.

The pack assembly is built around a backbone called the carrier, which serves as a support and handle for the other components. Preferably, a reservoir and an oxygenator are both physically but releasably attached to this carrier. Disposed around these central components, and attached to them in some way, will preferably be at least one tray. In preferred embodiments, two trays will be present, and it is considered particularly convenient that each of these trays be releasably attached to both the carrier and the reservoir. The carrier preferably has a handle so that the pack assembly can be easily moved and manipulated after being removed from its shipping container.

In preferred embodiments, various tubing assemblies will be pre-attached to the reservoir and the oxygenator, with the majority of their lengths conveniently coiled and disposed within the trays. Most conveniently, the trays will themselves be divided into several compartments, and tubes that share some functional relationship will be packaged together in the same compartment, separated from other tubes with different functions.

In particular, in one preferred embodiment there is a prime line for priming the reservoir prior to surgery. This prime line conveniently has a priming tube attached to the reservoir at one end and a bag spike at the other end. The end with the bag spike is disposed within a first compartment in one of the trays. It is particularly convenient if that tray has a narrow cut-out portion to admit the free end of the prime line so that the prime line may be deployed and attached to a bag of saline solution without first detaching the tray. In some embodiments, it is convenient that one or more of the tubes will have a grommet, and that grommet will allow the tube to pass through the cut-out portion in the wall of the tray while maintaining a sterile seal.

In similar fashion, an A-V loop, a pump loop, and one or more suction lines will be present in a preferred embodiment, and each group of lines will be packaged with most of their lengths within their own individual compartment within one of the trays. In the most preferred embodiments cut-outs are provided within the side walls of the trays so that each line or group of lines may be deployed before the trays are detached and discarded.

In the most preferred embodiment the trays hang vertically in the pack assembly, and a cover sheet is provided for each tray in order to keep the components within it enclosed. Any moderately sturdy sheet material should be suitable for the purpose, but a film of transparent polymeric material is considered particularly preferred so that the components within the trays can be inspected visually after assembly.

In a preferred embodiment of the invention, the pack assembly will include a barrier pouch enclosing all of its components. In the most preferred embodiment, the pack assembly is "self-contained," meaning that all the tubing and disposable elements necessary to connect a patient for bypass surgery is included in the pack.

BRIEF DESCRIPTION OF THE FIGURES

These, and other objects, features, and advantages of the present invention will become more readily apparent to those skilled in the art upon reading the following detailed description, in conjunction with the appended drawings in which.

DETAILED DESCRIPTION OF THE INVENTION

During preparation for a surgical procedure requiring cardiac bypass, the pack assembly of the present invention may be transformed from an undeployed configuration to a deployed configuration and used as part of an extracorporeal circuit. In the undeployed configuration, all of the disposable components of the extracorporeal circuit are either attached to a carrier or contained within a sealed tray associated with the carrier. To deploy the pack assembly for use, the trays may be attached or removed from the pack assembly and selectively opened, such that the desired tubing or pre-attached lines are uncoiled and positioned in their appropriate positions in the operating room.

Figure 1:
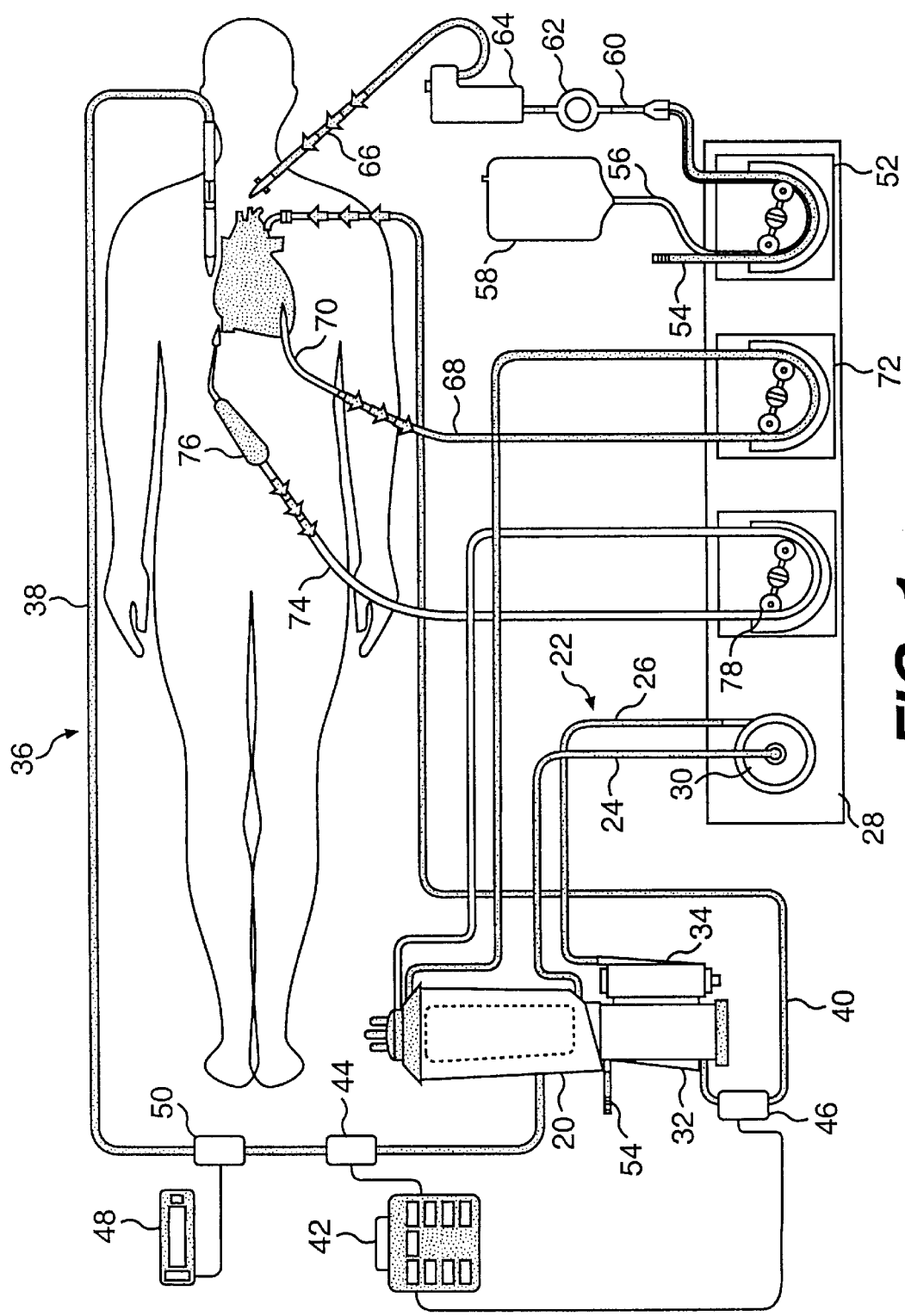
FIG. 1 is a schematic diagram showing a prior art extracorporeal support circuit.
Figure 2A:
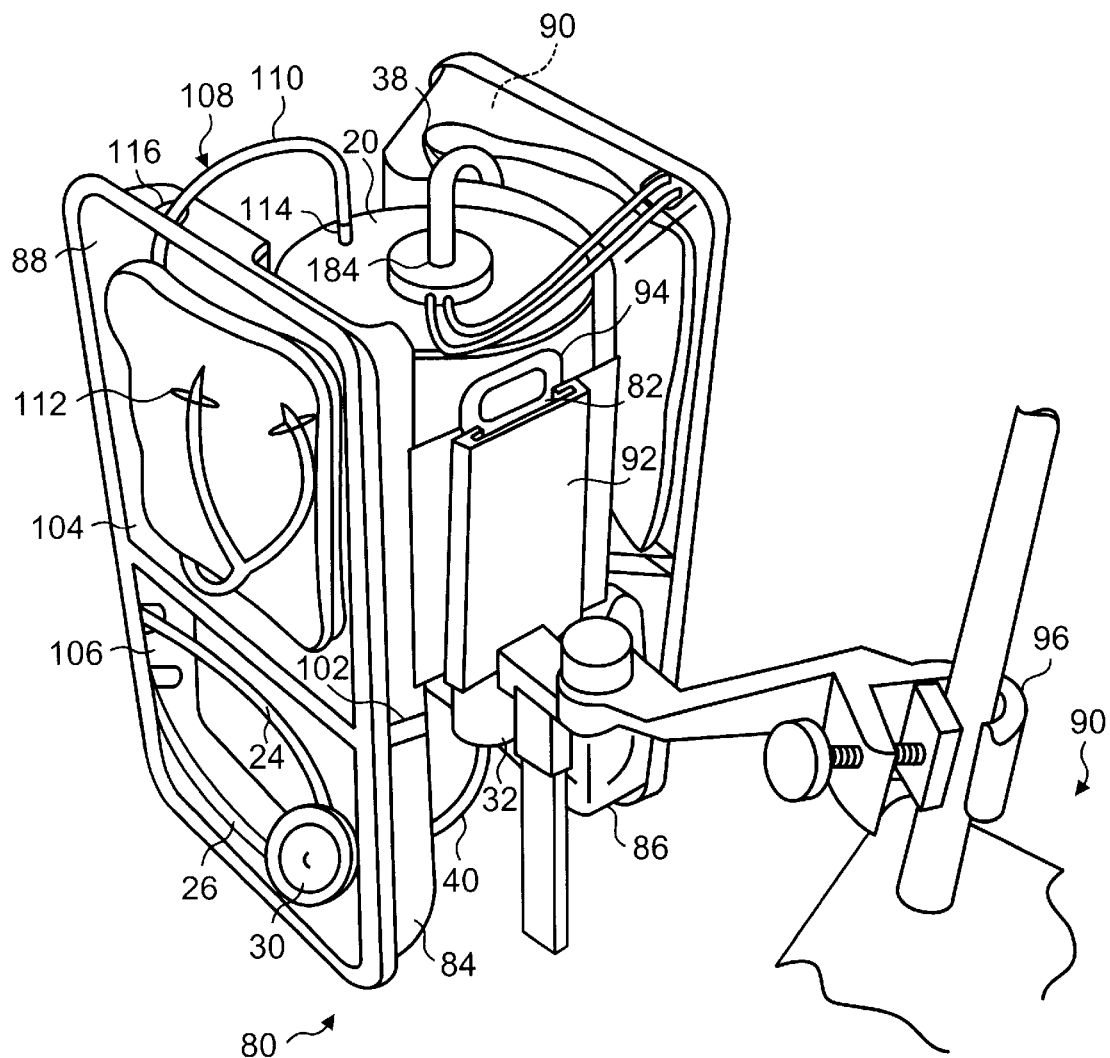
FIG. 2A is a perspective view of a preferred embodiment of the assembly pack of the present invention in an undeployed configuration.
Figure 2B:
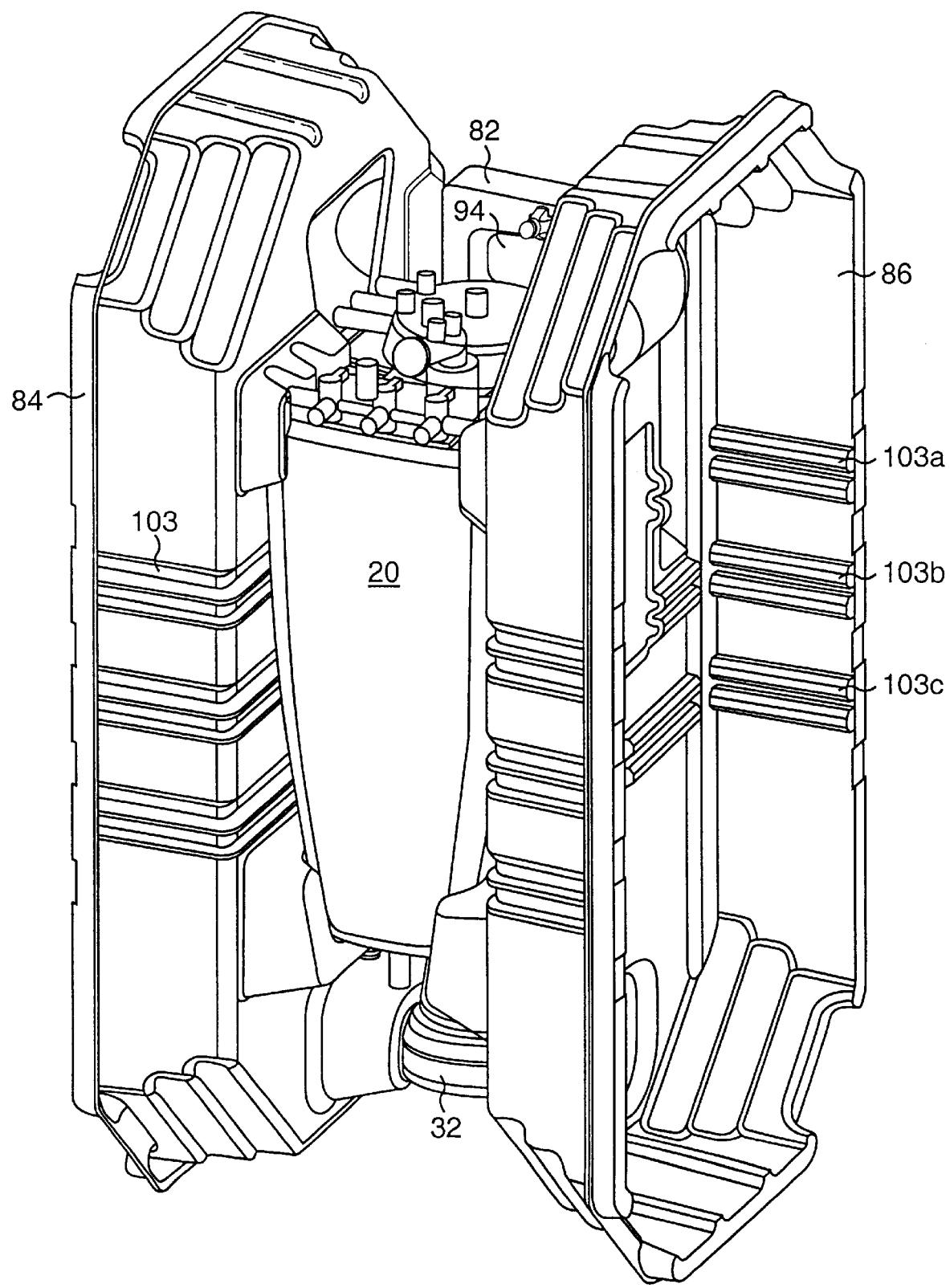
FIG. 2B is a perspective view of a further preferred embodiment of the assembly pack of the present invention.
Figure 3:
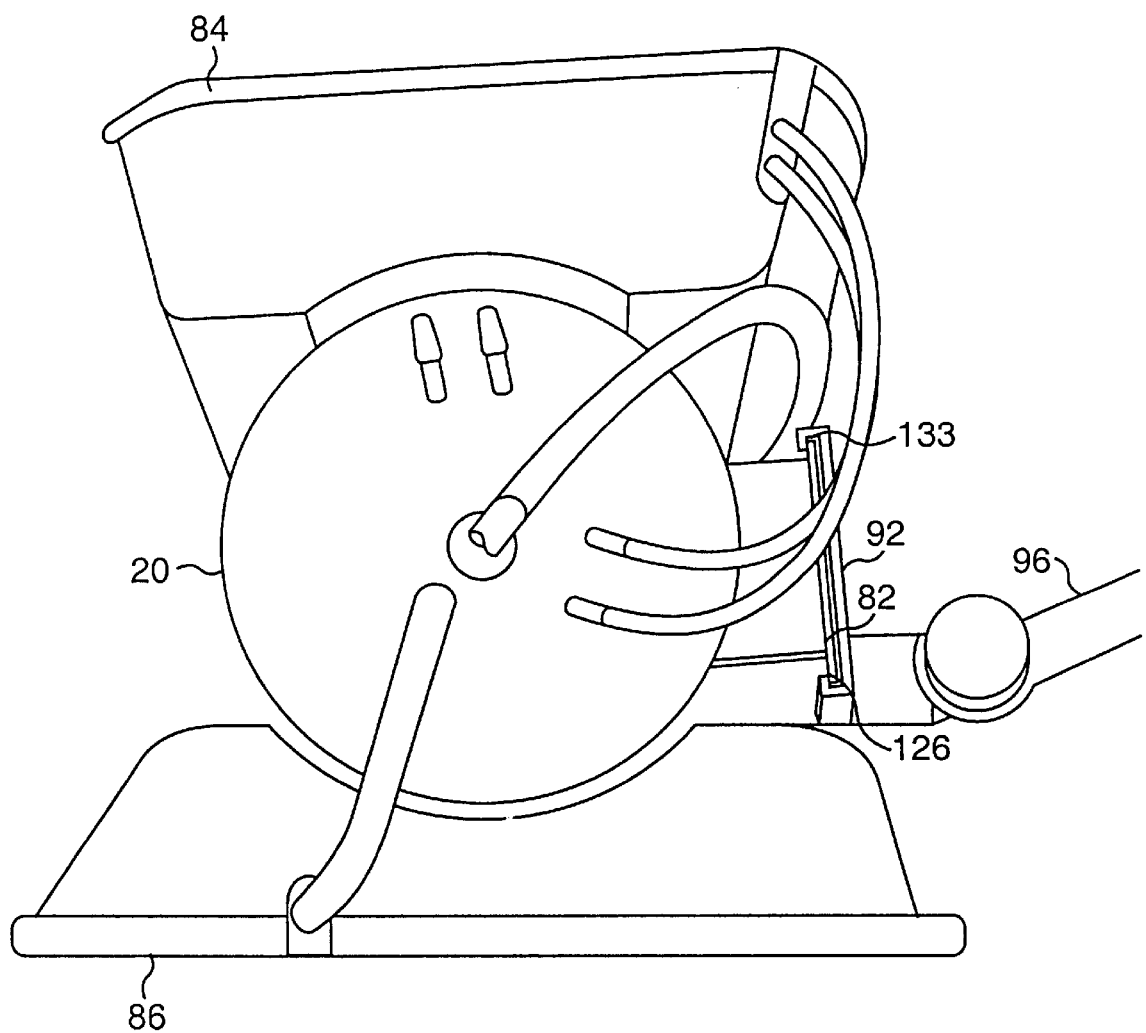
FIG. 3 is a top view of the assembly pack shown in FIG. 2A.
Figure 4:
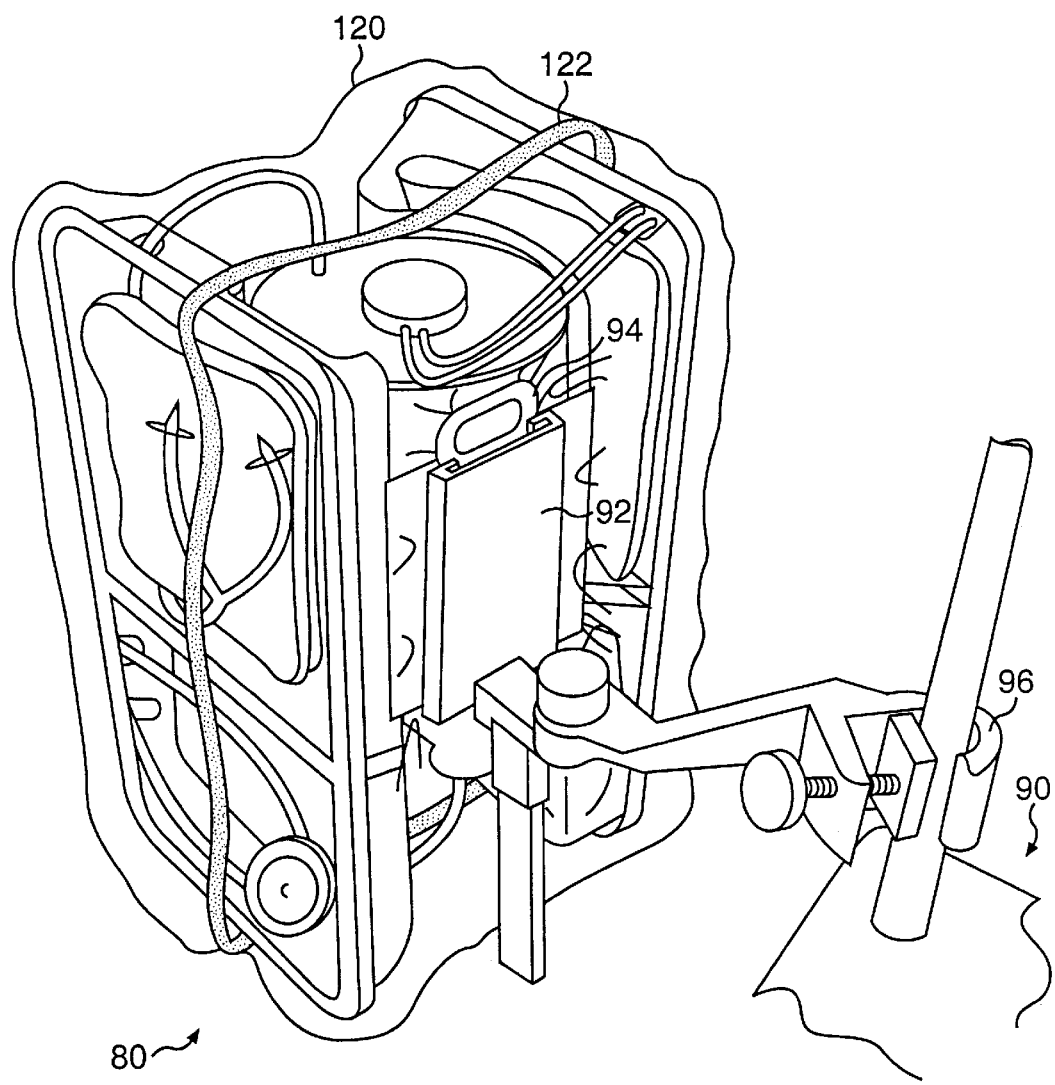
FIG. 4 is a perspective view of an alternative preferred embodiment of the assembly pack of the present invention in an undeployed configuration.

The undeployed configuration of a preferred embodiment of the pack assembly 80 is best shown in FIGS. 2–4. A blood reservoir 20 and a blood oxygenator 32 are preferably vertically mounted on carrier 82 with the blood reservoir 20 positioned on top of the blood oxygenator 32. Alternatively, however, it is within the scope of the present invention to only attach one of the reservoir 20 and the blood oxygenator 32 to the carrier 82. The carrier 82 includes a handle 94 for lifting and repositioning the pack assembly 80, and also includes two flanges 126 that may be slidingly engaged in channel 133 of the mounting bracket 92. Although the illustrated flanges 126 are vertically disposed, it is within the scope of the present invention to provide for horizontal attachment between the carrier and mounting bracket. Clamp 96 attaches the mounting bracket 92 to a stand assembly 90 and vertically suspends the pack assembly 80 at a height selected by the operator for use during a surgical procedure. In the preferred embodiment, the stand assembly includes the vertical mast of a heart lung machine. However, the pack assembly may optionally be attached to any vertical support structure at a selected height, such as for example a bench or ledge.

The pack assembly 80 may include at least one tray, and more preferably, two trays 84, 86 which are most preferably attached to the carrier 82. The trays are preferably thermoformed of a transparent or translucent plastic so as to allow the technician to view the contents, while still retaining sufficient rigidity for shipping, storage and use. The trays 84, 86 may be attached by hook and loop fasteners, by an adhesive or by any means known to those in the art. Although attachment to the carrier 82 is most preferred, the trays may also/alternatively be attached to either the reservoir 20 and/or the oxygenator 32. In a preferred embodiment, the trays 84, 86 have small rivets which connect the trays to the carrier 82 and a further barb may optionally be provided for cooperation with a preformed hole 161 (shown in FIG. 7A) in the blood reservoir 20. The trays 84, 86 are sized and shaped to partially enclose the reservoir 20 and oxygenator 32, and may be divided into one or more compartments for organizing and holding individual subsystems or coiled lines until needed for use. The trays preferably may have cut-out portions 116 through which one end of a stored line may be extended for attachment to another component in the system. If sterility of the components stored within the trays is desired, the cutout portions 116 may be lined with grommets in order to provide a better seal between the tray and the tubing and thereby maintain the sterility of the tray. Further, in addition to providing an improved and convenient means for packing the needed tubing, the trays 84, 86 provide a protective packaging which surrounds the oxygenator and/or reservoir and serves to protect the same. Further, after use of the oxygenator and blood reservoir, the trays 84, 86 form convenient tubs or bins for use in disposal of the used tubing and other equipment.

As shown in FIG. 2A, the first tray 84 may be divided by partition 102 into an upper compartment 104 and a lower compartment 106. Preferably, partition 102 is also transparent or translucent and is removably and slidably disposed within any one of a plurality of partition guides 103a, 103b, 103c, as shown more clearly in FIG. 2B. The partition guides 103 allow each tray to be customized per a customer's specifications as to the number and size of compartments to be configured in each tray, anywhere from one compartment on up being foreseeable in accordance with the present invention. While the partitions 102 are illustrated as extending transversely across the trays, it is foreseeable that partitions in the longitudinal direction could also be used, as could partition planes for layering the contents of the tray from the inner side of the tray to the exposed outer side. A cover sheet 88 is sealed over the opening of the tray to maintain sterility or, more preferably, to merely prevent the tray's contents from spilling out of the tray before the pack assembly 80 is deployed for use. Alternatively, a cover 88' as shown in FIGS. 1A–11C may be provided.

For the embodiment shown in FIG. 2A, the upper compartment 104 contains a priming line 108 that includes a pair of bag spikes 112 and a priming tube 110 that extends through a cut-out portion of the tray 84 and attaches to the reservoir 20 at prime port 114. When the pack assembly is deployed for use, the prime line 110 will deliver saline solution to the reservoir to prime the system. The lower compartment 106 contains a pump loop including a pump inlet line 24, a pump outlet line 26 and a pump header 30. The pump lines 24, 26 extend through cutouts and attach to the reservoir 20 or oxygenator 32.

The second tray 86 preferably also includes at least two compartments. One of the compartments may include an A-V loop, including a venous line 38 and an arterial line 40, shown in FIGS. 8 and 9. Portions of the venous line 38 and arterial line 40 are preferably extended through cut-outs in the tray compartments to attach to other components in the system. The other compartment of the second tray 86 preferably includes a suction line, such as suction lines 152 and 154, shown in FIGS. 8–9, a portion of which is extended through a cut-out portion of the tray and attached to the reservoir 20.

The above-described components within each tray 84, 86 are merely examples. One of the advantageous features of the present invention is that each tray may be customized to contain the tubing and/or other components desired by the customer based upon their particular operating room protocol. As a further example, one tray could contain all of the tubing necessary for set-up, i.e., the A-V loop, the arterial pump loop, and the prime line, while a second tray contains the remaining tubing, i.e., suction lines, cardioplegia lines, and any other desired components, such as a hemoglobin concentrator, or the like. Of particular note in the present invention, is that the various tubing lines are vertically stacked within the tray so as to enable easy deployment of one group without unnecessarily removing another. Further, although the above-described embodiment includes premade connections between the various tubes and the oxygenator and/or reservoir and/or other components, the number and type of pre-made connections which are attached are once agin the customer's choice depending upon their particular operating room protocol. As a further example, with respect to the number of pre-made connections to be made, one tray could include all the lines which are to have pre-made connections, and the remaining tray may include all the tubing lines which do not have pre-made connections. In addition, while the trays 84, 86 are preferably configured for exposing their contents on an exterior of the pack assembly, it is within the scope of the present invention to provide trays which face inward, in which instance it would be necessary to remove the trays from the pack assembly prior to deployment of selected tubing groups.

The cover sheet 88 for the trays 84, 86 is preferably made of a flexible polymeric material, and most preferably of a transparent flexible polymeric material that allows a person who is deploying the circuit to see which components are in the compartments before removing the cover material. The cover sheet 88 may be attached to the edges of the trays 84, 86 by an adhesive, by heat sealing or by any method known in the art for sealing a polymeric material to another surface. Of particular preference is a releasable and resealable adhesive which would allow operating room personnel to quickly deploy a selected tubing group and then reseal the cover sheet until the remaining groups or equipment are to be connected. For this reason, among others, it is particularly desirable to have a transparent cover sheet 88. While cover sheet 88 is not intended to preserve sterility, it is within the scope of the present invention to provide a cover seal which would be capable of preserving the same.

Figure 11A:
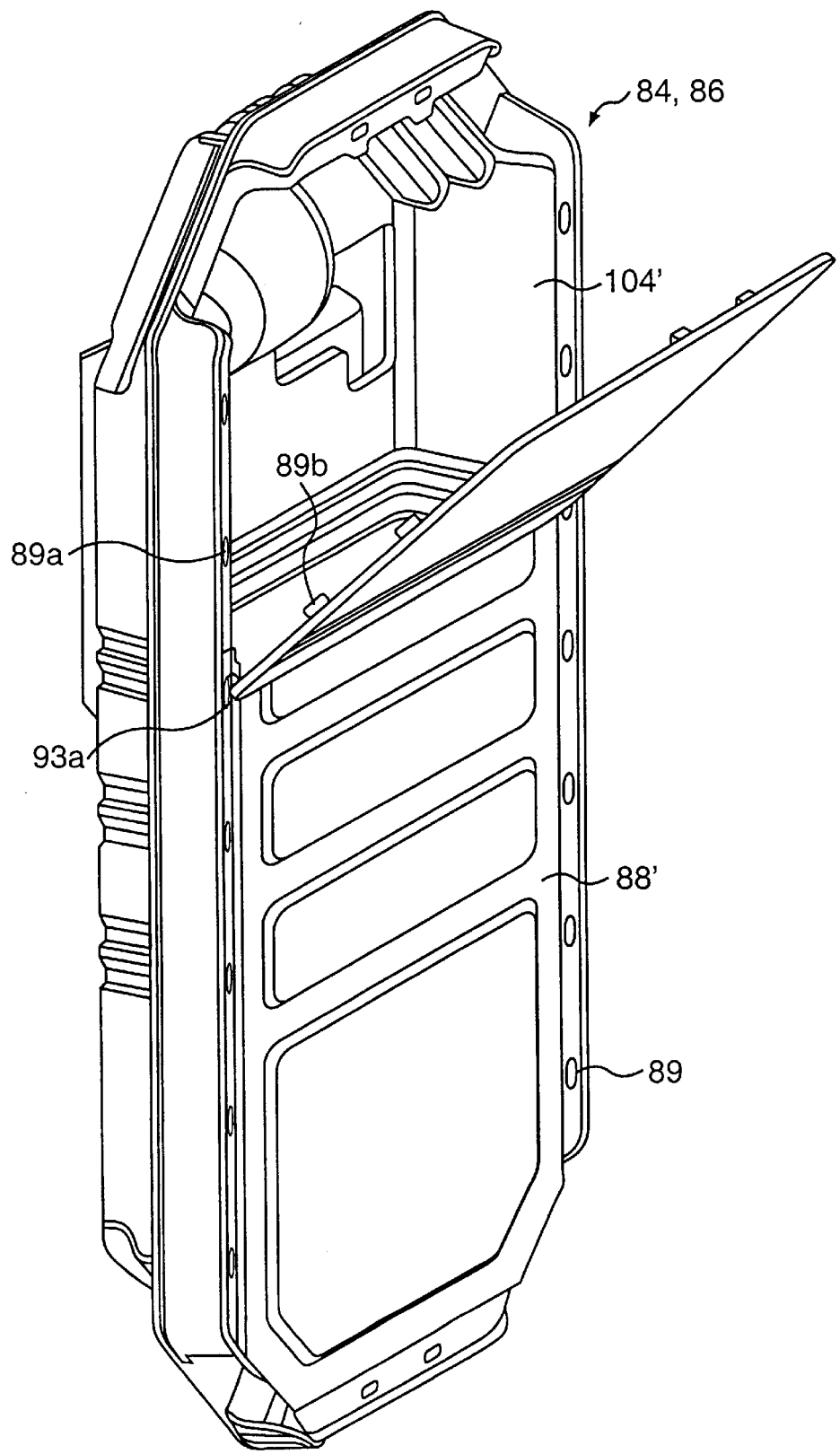
FIGS. 11A–11C are perspective views of the tray assembly shown in FIG. 2B, with an alternative embodiment cover according to the present invention.
Figure 11B:
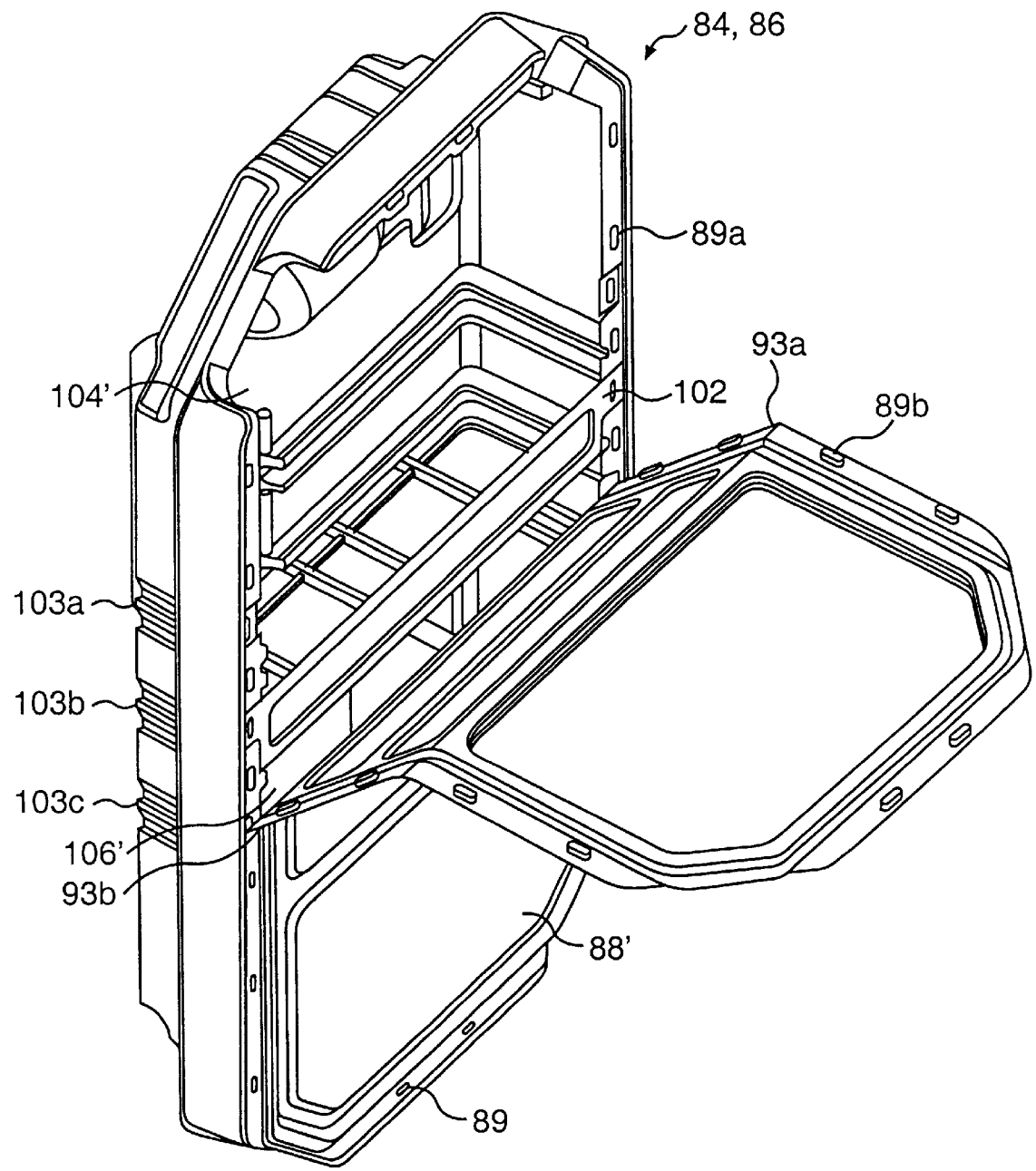
Figure 11C:
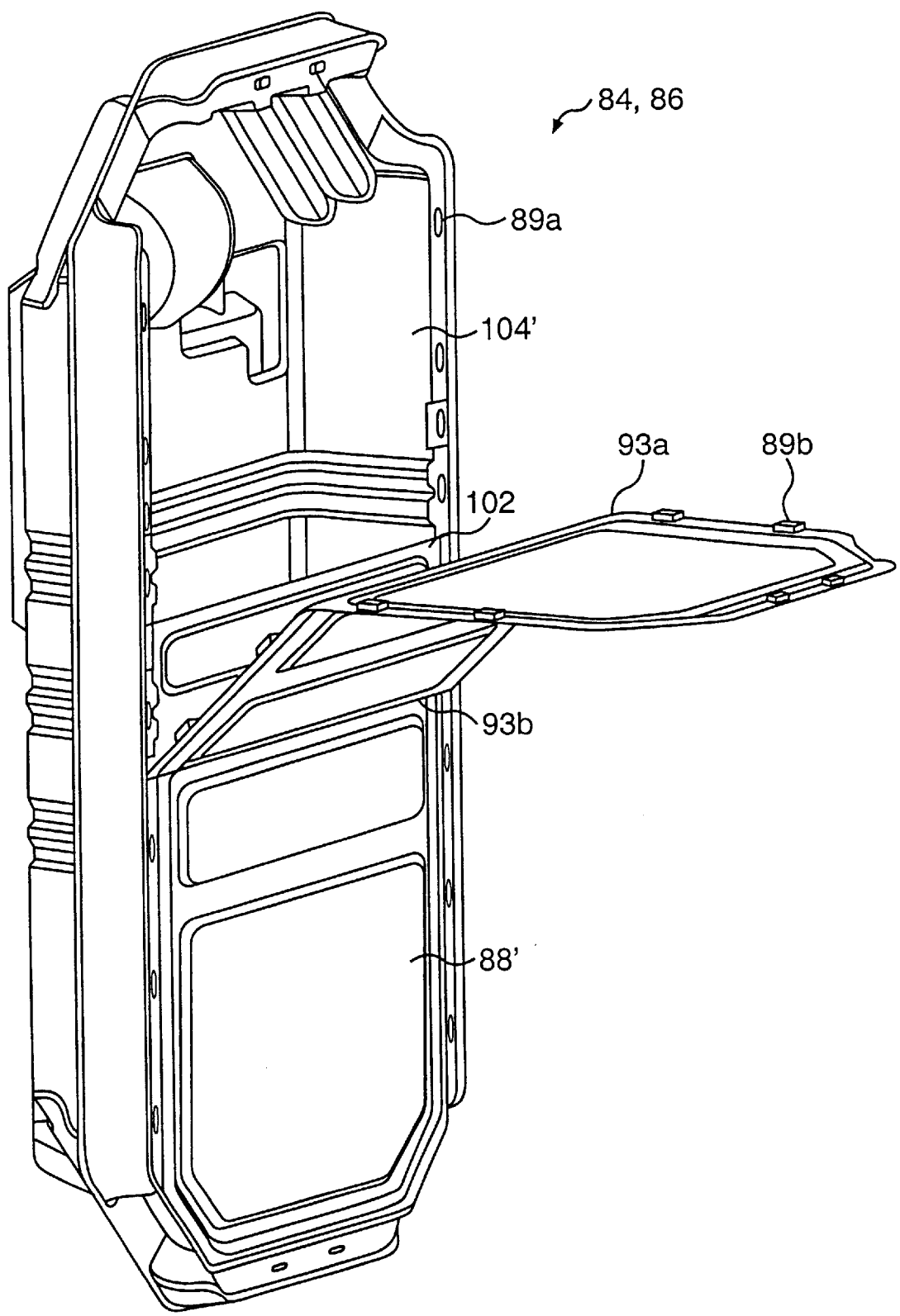

The cover 88' shown in FIGS. 11A–11C provides an additional advantage in that one compartment may be easily exposed and the contents thereof removed without exposing or disturbing the remaining compartments within the tray 84, 86. The cover 88' is preferably a flexible and transparent thermoformed plastic which has a greater rigidity than the cover sheet 88 described above. It may be attached to the periphery of the tray 84, 86 through a plurality of snap type locks 89 disposed about the outer perimeter of the cover 88'. The snap type locks 89 are known in art and generally include male/female interengagement portions 89$a$ and 89$b$. It should be apparent to one skilled in the art that other types of sealing mechanisms, preferably recloseable, could of course also be used, such as, for example, rivets, a continuous tongue and groove engagement around the perimeter or other common plastic blister pack seals. The uppermost compartment 104' of the tray shown in FIGS. 11A is exposed by detaching several top and side snap locks 89. The cover 88', due to its flexible nature, is then able to fold backwards along a hinge line 93$a$ which will be formed during the opening process. When the cover 88' is further opened, as shown in FIGS. 11B and 11C, an additional hinge line 93$b$ may form so as to expose a second compartment 106', while still securely covering the remaining lower compartments. Although cover 88' is illustrated as opening from the top to the bottom of the tray, it should be clear that cover 88' could easily be opened in the opposite direction as well. Further, while FIGS. 11A–11C refer to tray 84, 86, it should be understood that it is possible for only one tray to be provided with the cover 88' and that only one tray may have more than one compartment, depending upon the customer's specifications. Similarly to the above-described cover sheet 88, cover 88' is not intended for preserving sterility, but it is deemed within the scope of the present invention to accomplish the same.

Figure 6A:
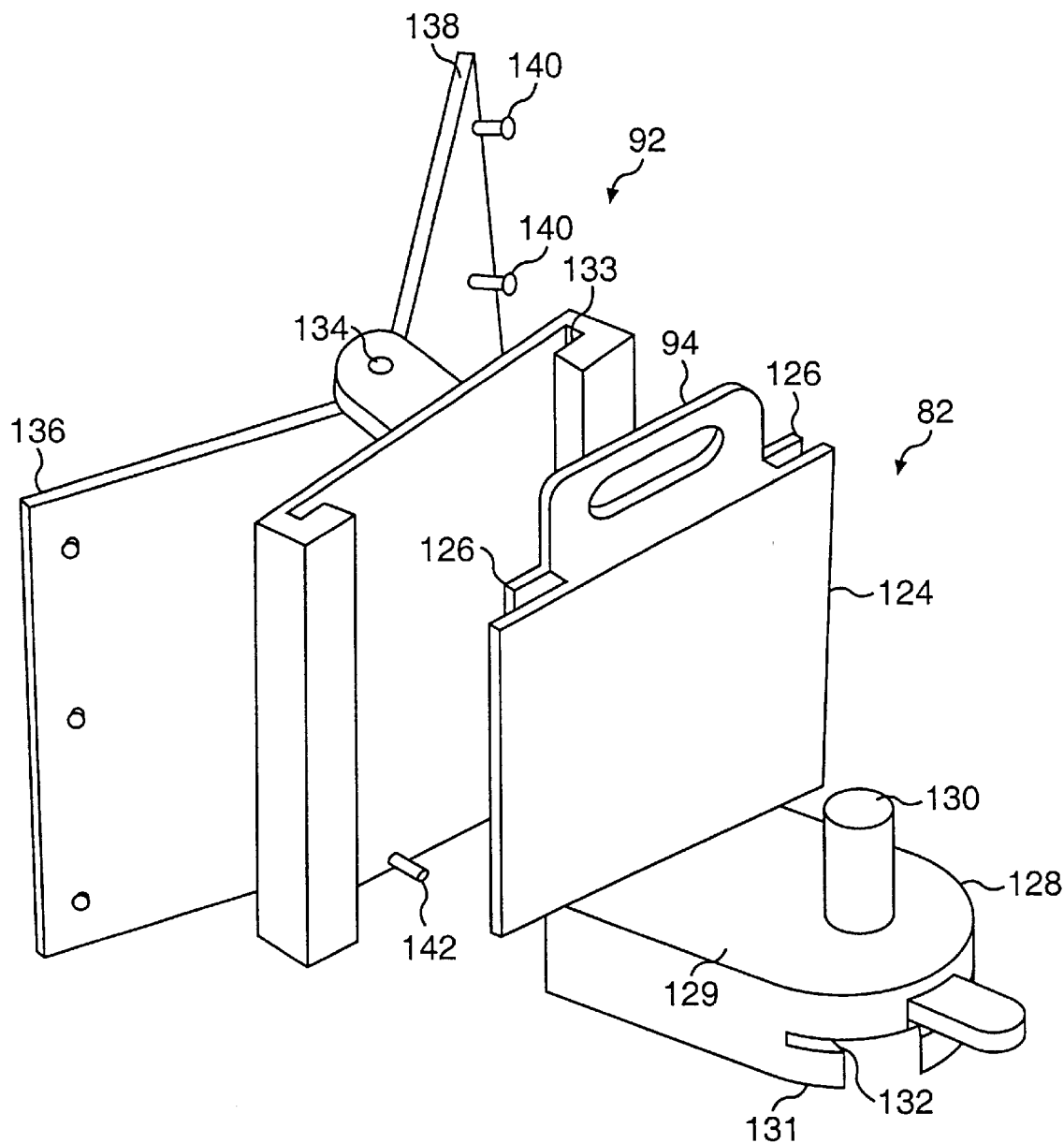
FIG. 6A is a perspective view of the carrier and the mounting bracket shown in FIGS. 2A–4.

As best shown in FIG. 4, the pack assembly 80 may also include a barrier pouch 120 that completely encloses the blood reservoir 20, the blood oxygenater 32 and the carrier 82. The barrier pouch 120 preferably serves to maintain the sterility of the components of the pack assembly. In the preferred embodiment, the pack assembly may be attached or detached from the mounting bracket 92 without removing the barrier pouch 120. The barrier pouch may be constructed of two pieces joined together by a sealing strip 122, which forms a continuous hermetic seal and which facilitates easy removal of the barrier pouch when the pack assembly 80 is needed for use. The barrier pouch is preferably made of a flexible polymeric material, and most preferably is made of a transparent flexible polymeric material. The sealing strip 122 may be formed, for example, by hot plate sealing so as to actually melt the two sheets together at the seam and form a non-permeable joint, or by any means known by those in the art for hermetically joining together pieces of polymeric sheet material. Alternatively, the barrier pouch 120 may be a sealed enclosure which is cut or otherwise torn away when the pack assembly is to be used. Any remaining pouch material lodged between the mounting bracket 92 and the carrier 82 does not effect the performance of the pack assembly and can therefore be disregarded. In particular, providing tapered flanges 126' as shown in FIG. 6D and a correspondingly tapered receiving channel (not shown) in the mounting bracket allows the barrier pouch 120 to sufficiently deform, without tearing, such that the pack assembly may be mounted on an operating room stand prior to use while still maintaining the sterility thereof.

The pack assembly 80 has so far been described with reference to an embodiment that includes two trays. However, the pack assembly may include any number of trays that is reasonable given the size and shape of the reservoir and oxygenator, and all such variations are considered to be within the scope of the invention. For example, in one embodiment, separate trays may be provided instead of separate compartments in a larger tray, which may double or triple the number of trays used in the pack assembly. In another embodiment, trays may be placed on the top and bottom of the pack assembly 80 in addition to or instead of the trays on the side or sides of the pack assembly 80. Further still, a single tray may be formed in a U-shaped configuration so as to surround both sides and the top or bottom of the pack assembly. Given the possible combinations suggested by the invention, the pack assembly of the invention may include a single tray or as many as ten or more trays.

Figure 7A:
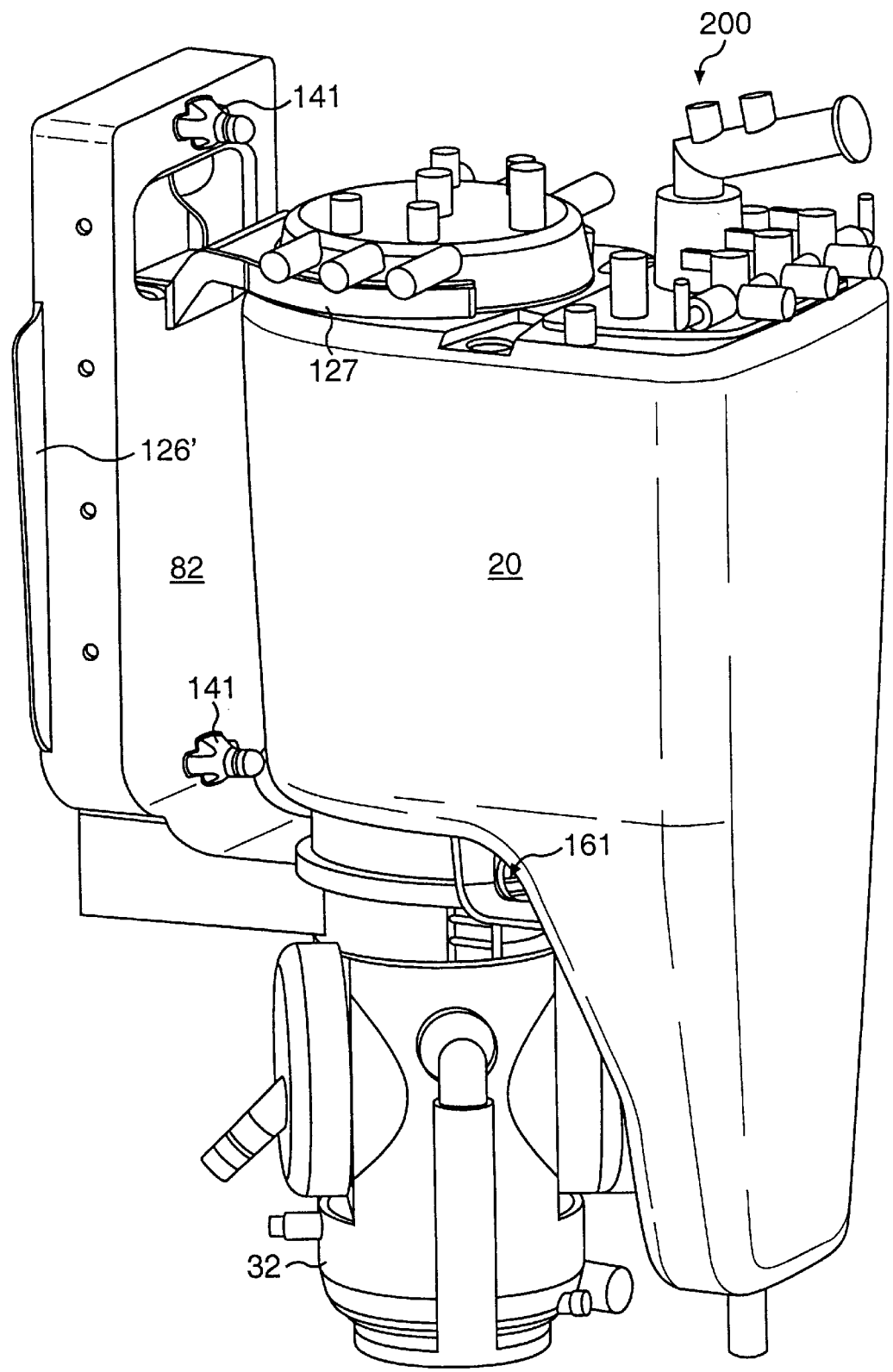
FIG. 7A is a side view of a preferred embodiment of the assembly pack of the present invention.
Figure 7B:
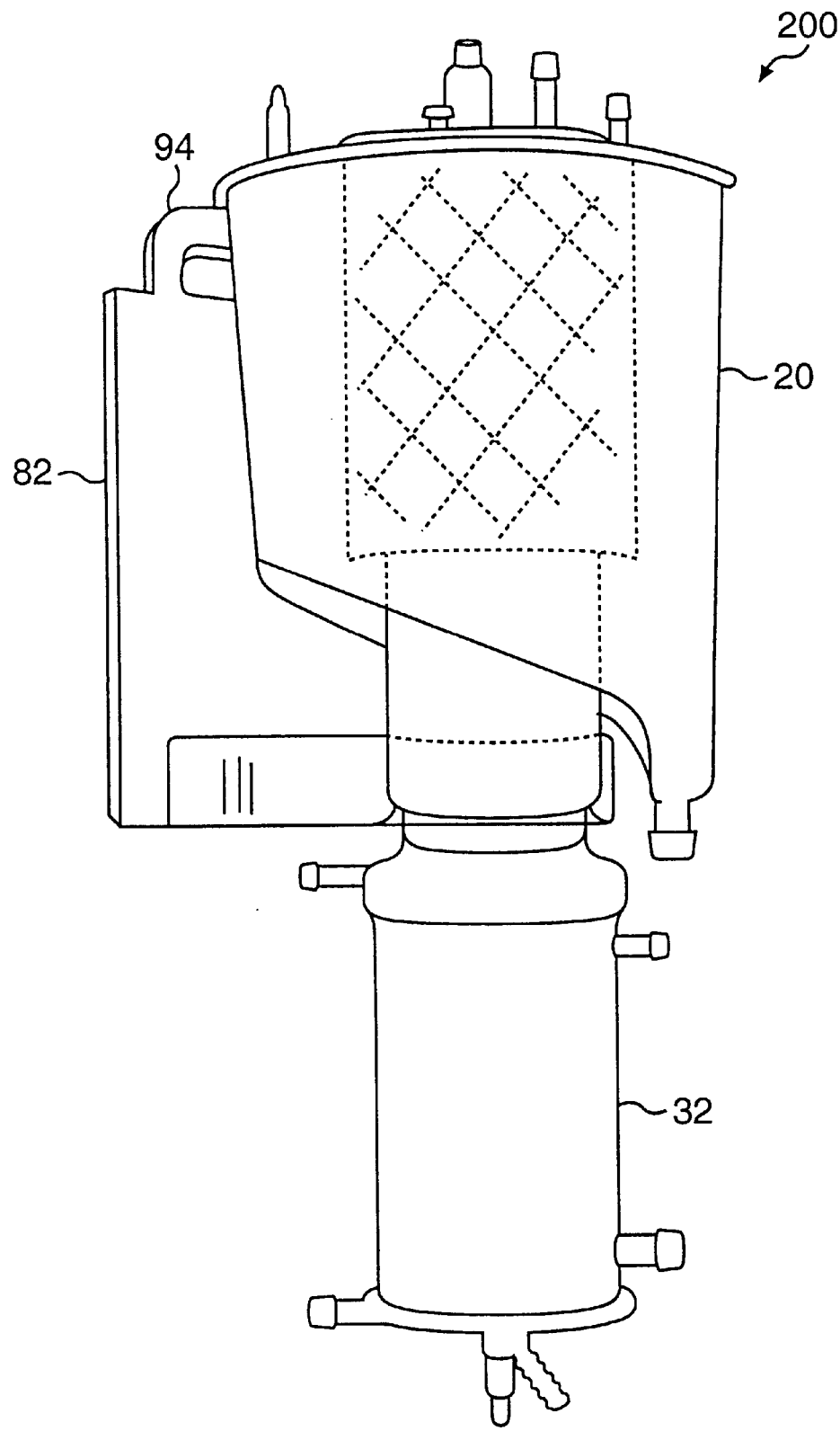
FIG. 7B is a side view of a further preferred embodiment of the assembly pack of the present invention.

The present invention also envisions the use of the carrier 82 without any trays, as best shown in FIGS. 7A and 7B. Pack assembly 200 includes the carrier 82, the blood reservoir 20 and the blood oxygenator 32. Even without attaching the trays, this embodiment provides an advantage in that it allows the blood reservoir 20 and blood oxygenator 32 to be vertically mounted and easily moved during surgery. More importantly, the carrier 82 of the present invention allows the separate and independent attachment of the blood reservoir 20 and the oxygenator 32 within a circuit, resulting in a fixed arrangement in which the blood reservoir 20 and the oxygenator 32 are not directly fluidly connected to one another, as will be described in greater detail below. Although the illustrated embodiment does not include the inventive trays of the present invention, it is nevertheless foreseeable that the necessary tubing connections can be pre-made and the tubing merely coiled around the assembly 200, or otherwise attached to the carrier, blood reservoir and/or oxygenator, which is then wrapped in a protective barrier pouch until ready for deployment. In this instance, it would likely be necessary to provide foam blocks, thermoforms, or the like to provide protective packaging to the assembly 200. It is also within the scope of the present invention to provide such type of protective packaging around the assembly 200, and then encasing the same in a barrier pouch to preserve sterility. Still further, although the vertical mounting of the blood reservoir and the oxygenator is preferred, it is also feasible to provide for a telescoping connection between the blood reservoir and the oxygenator and/or a two-part carrier 82 so as reduce the space requirements for shipping, and requiring only minimal adjustments to achieve the preferred vertical mounting during set-up.

Figure 5:
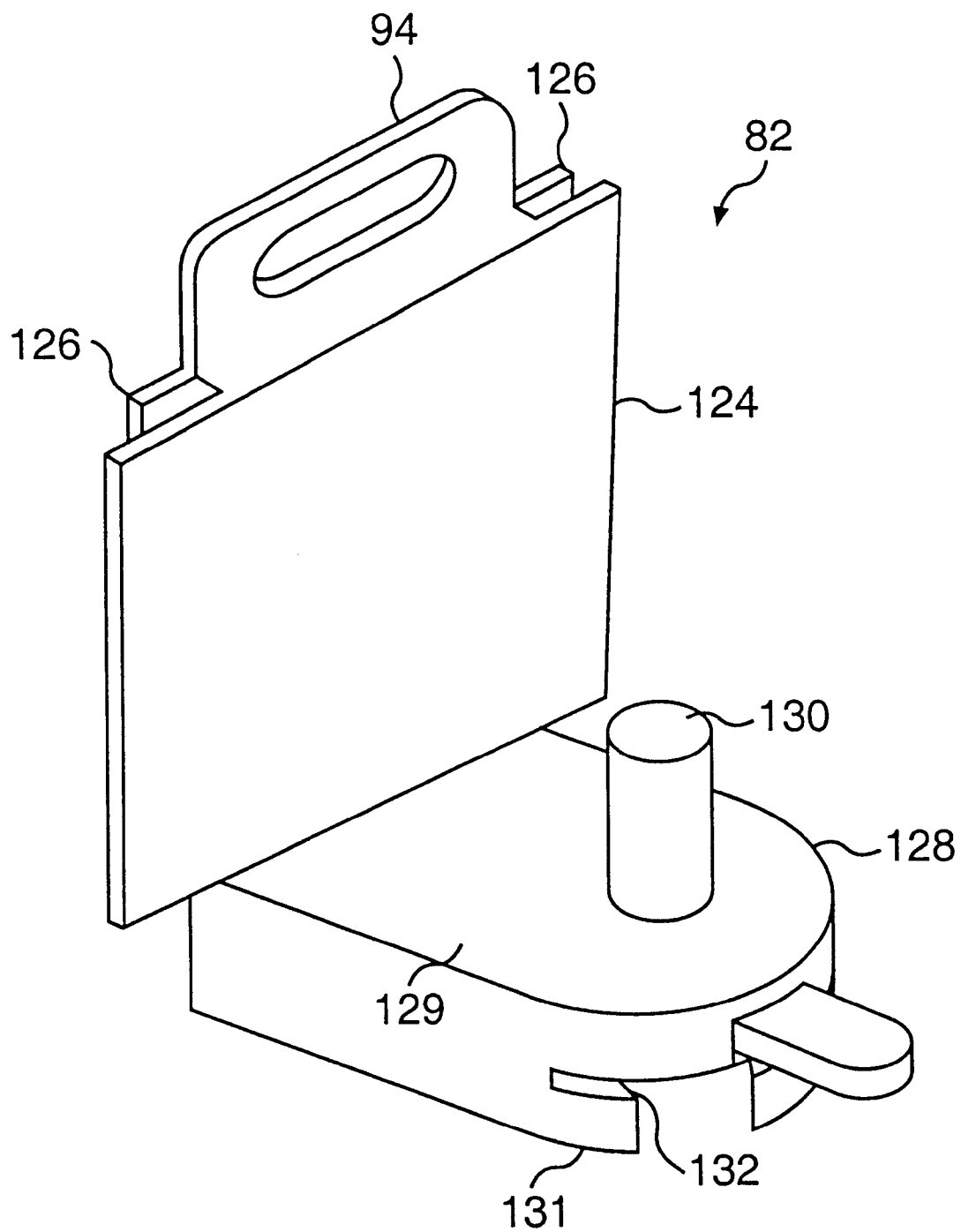
FIG. 5 is a perspective view of the carrier shown in FIGS. 2A–4.

The structural detail of the carrier 82 and the mounting bracket 92 used in the pack assembly 80 are best shown in FIGS. 5–6. The carrier 82 includes a substantially horizontal attachment plate 128 and a substantially vertical mounting plate 124. These plates may be separately made pieces that are joined together, or more preferably may be parts of a single molded piece, as shown in FIG. 6C. The attachment plate 128 is adapted to support one blood handling apparatus on its top surface 129 and to suspend another blood handling apparatus from its bottom surface 131. The blood handling apparatus supported on the top surface 129 is preferably a blood reservoir or a blood oxygenator, and most preferably is a blood reservoir. The blood handling apparatus suspended from the bottom surface 131 is preferably a blood reservoir or a blood oxygenator, and most preferably is a blood oxygenator.

Each of the two blood handling apparatuses supported by carrier 82 may be separately and independently added or removed from the carrier without disturbing the other blood handling apparatus from the carrier. For instance, if it becomes necessary to replace a blood reservoir 20 during surgery, it may be removed from the carrier 82 without removing the blood oxygenator 32. A blood oxygenator 32 may also be removed from the carrier 82 without removing the blood reservoir 20.

The top surface 129 of the attachment plate 128 may preferably include a retention peg 130 that is sized and shaped to fit into a mating recessed portion in the bottom of a blood reservoir and thereby hold it securely in place. Further, a stabilizer clip 127 may optionally be provided (as shown in FIG. 7A) to provide further security against vibration, which is particularly preferred when a roller pump is to be used. The retention peg 130 is suitable for use with hard bodied blood reservoirs, such as reservoirs that combine the functions of cardiotomy blood filtration and venous blood reservoir. However, the retention peg may be advantageously removed when a soft blood reservoir bag is used in the system. In addition to the retention peg, or as an alternative to it, the reservoir may be held in place by a hoop shaped clamp attached to the vertical mounting plate 124. The lower surface 131 of attachment plate 128 includes a channel 132 for receiving and securely retaining a disk attached by a stem to a blood handling apparatus. In one preferred embodiment, the blood handling apparatus is a blood oxygenator and the channel-disk attachment apparatus of attachment plate 128 is the apparatus described in commonly assigned U.S. application Ser. No. 08/962,360, now U.S. Pat. No. 5,958,338, the contents of which is incorporated herein by reference.

Figure 6B:
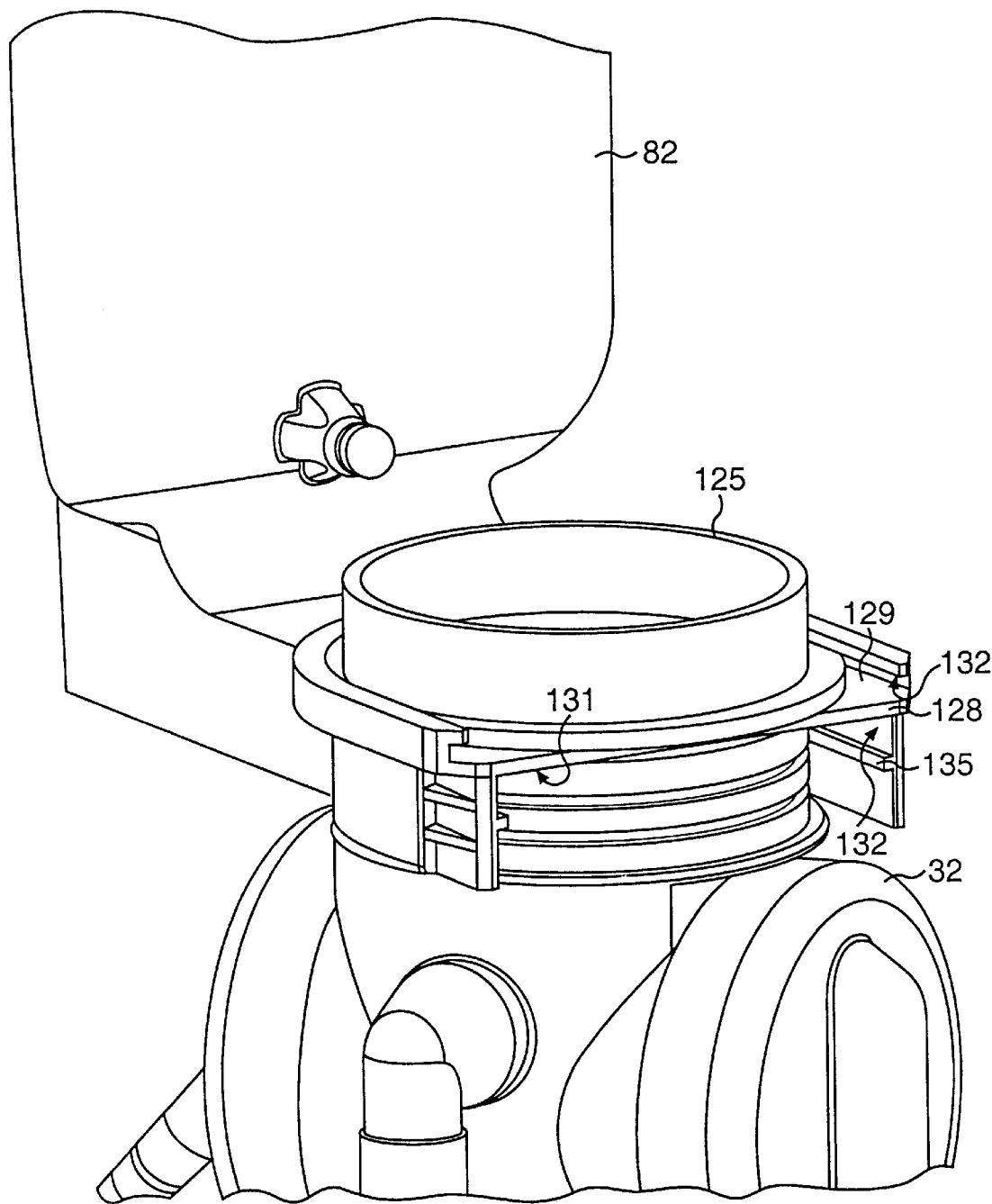
FIG. 6B is a perspective view of an alternative preferred embodiment of the carrier.
Figure 6C:
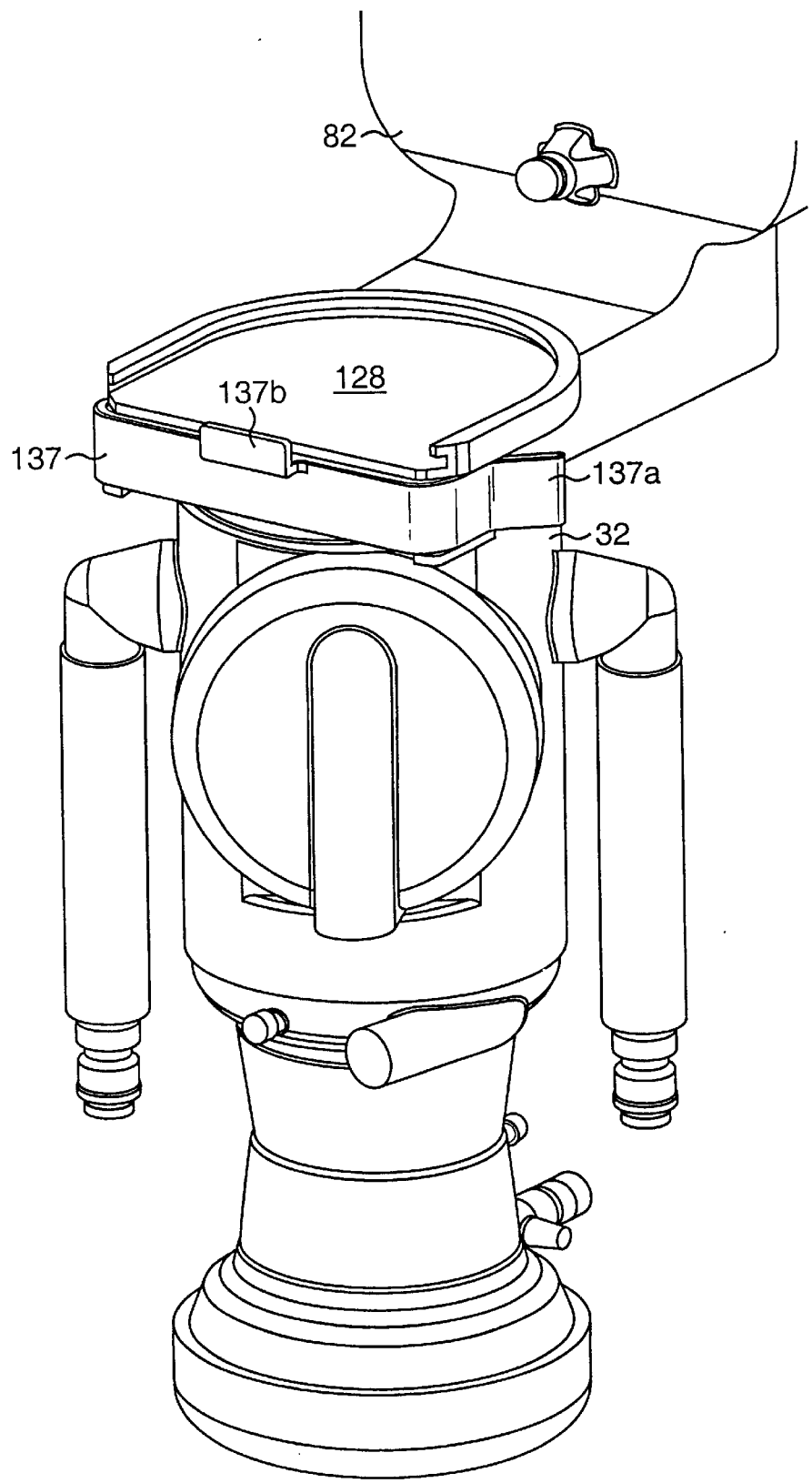
FIG. 6C is a further perspective view of the carrier shown in FIG. 6B.
Figure 6D:
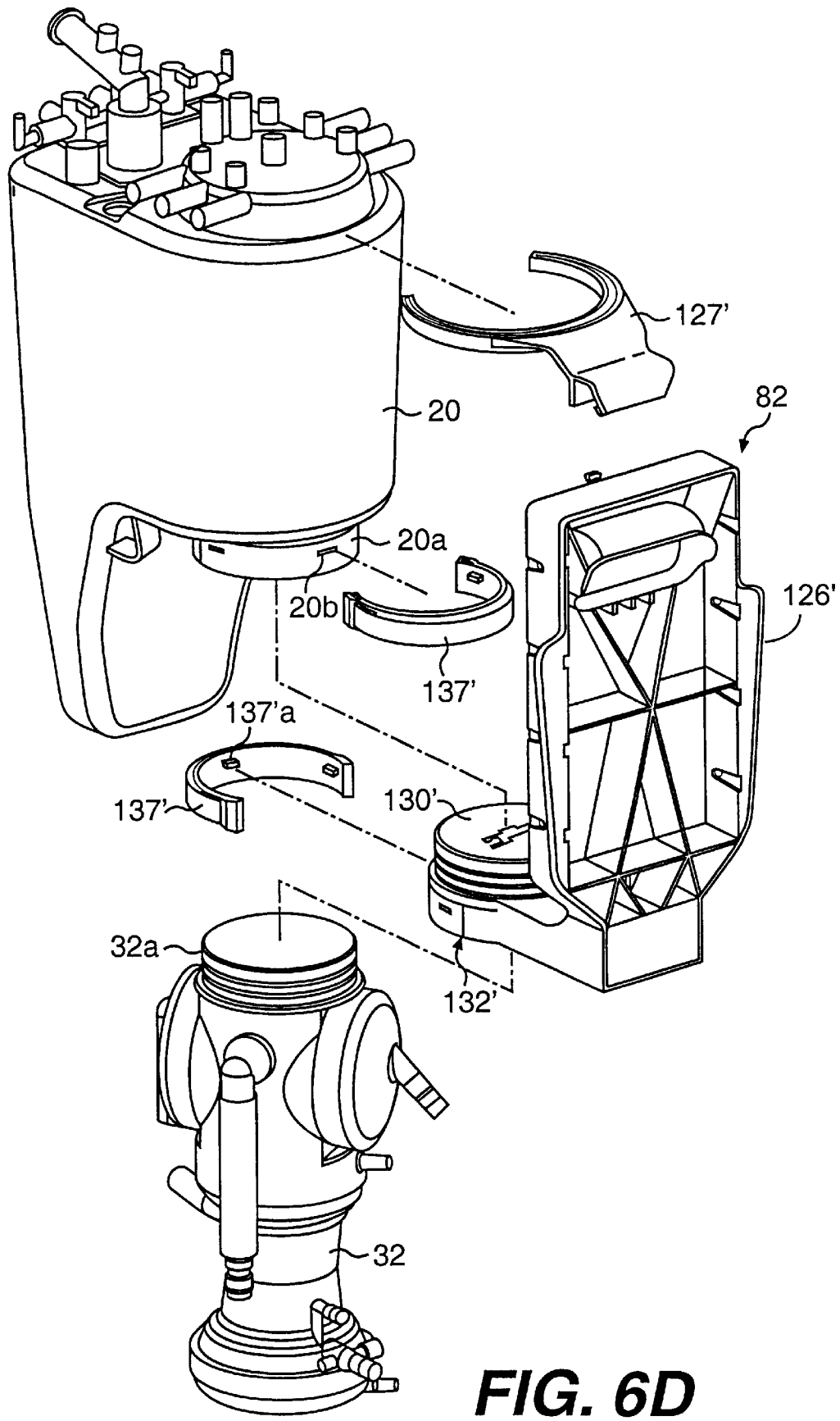
FIG. 6D is an exploded perspective view of an alternative preferred embodiment of the carrier.

Alternatively, as shown in FIGS. 6B and 6C, a further embodiment of the carrier 82 has a top surface 129 of the attachment plate 128 which may include a channel 132 for laterally receiving and securely retaining a disk or an adapter flange 125 that may be bonded, snapped, or otherwise attached to an upper blood handling apparatus, such as blood reservoir 20 (which is not shown for clarity). The channel 132 defined on the lower surface 131 of the attachment plate 128 may include an internal circular ring 135 which cooperates with and is seated within an annular groove provided on the upper rim of the lower blood handling apparatus, such as blood oxygenator 32, which is laterally moved into the proper position. As illustrated in FIG. 6C, the present invention further provides a retainer bar 137 that may be used to retain one or both of the upper blood handling apparatus, such as reservoir 20, and the lower blood handling apparatus, such as oxygenator 32, within their respective positions. The retainer bar 137 preferably includes projecting barbs (not shown) on the rear surface thereof which positively engage the carrier 82. The presence of the retainer bar 137 further increases the stability of the blood handling apparatuses during surgical procedures and decreases the likelihood that the reservoir 20 or the oxygenator 32 will be accidently removed. As shown, the retainer bar 137 preferably includes outwardly projecting thumb tabs 137a which assist operating personnel in quickly locating the retainer bar 137 and removing the same prior to removal of the oxygenator and/or blood reservoir. The retainer bar 137 also may include an upwardly projecting tooth 137b which, in addition to preventing the removal of the upper blood handling apparatus, provides a means for indexing the rotation of the upper blood handling apparatus so as to ensure that it obtains a secure detent position.

Figure 6E:
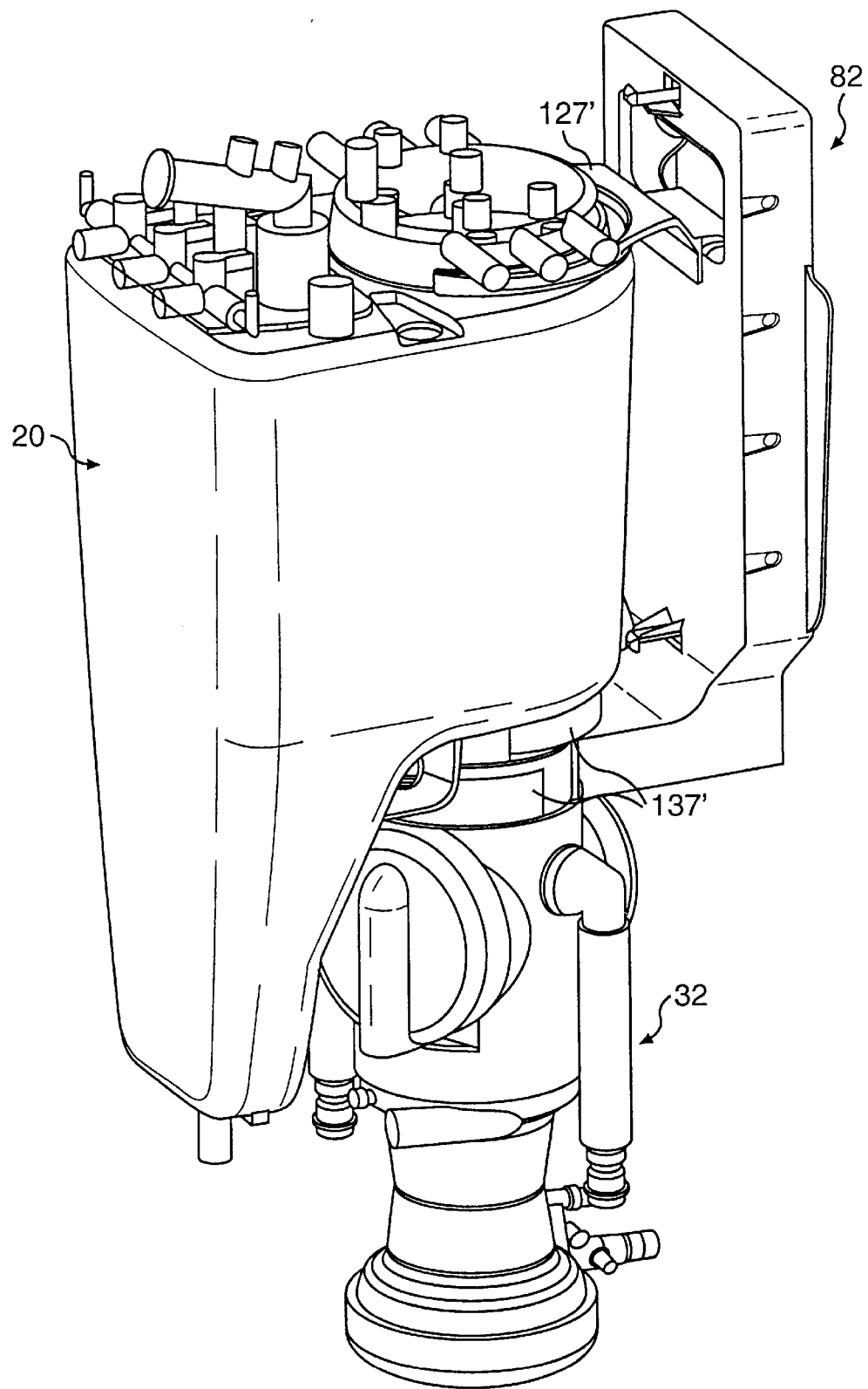
FIG. 6E is an assembled perspective view thereof.

Still further, referring to FIGS. 6D and 6E, an alternative attachment configuration which may be utilized includes a cylindrical boss 130' extending from the top surface 129 of the carrier plate 128. The configuration of the cylindrical boss 130' corresponds to a known cylindrical boss fitting 32a on the upper surface of the oxygenator 32. Thus, the lower mating socket 20a of the blood reservoir 20, which heretofore would be connected directly to the oxygenator 32, may now be connected instead to the cylindrical boss 130' of the carrier 82 without requiring any design changes. Similarly, the lower surface 131 of the carrier plate 128 may include a socket or recess 132' configured for receiving the cylindrical boss fitting 32a on the upper surface of the oxygenator 32.

When the oxygenator and blood reservoir are assembled into position on the carrier 82, a pair of C-clips 137' are preferably utilized to fasten each respective blood handling apparatus to the carrier 82 and to prevent unwanted or accidental removal of the oxygenator or the blood reservoir. Each clip has a plurality of projecting teeth 137' a which are received through holes 20b in the reservoir socket 20a and into the grooves of the cylindrical boss 130' of the carrier 82. A stabilizer bridge 127' may also be provided to grip the reservoir 20 and connect to the carrier 82 while still allowing rotation of the reservoir.

As set forth above, various embodiments have been described for providing a connection between the oxygenator and the carrier and between the reservoir and the carrier. As should be apparent to one skilled in the art, any disclosed connection embodiment for the reservoir may be combined with any disclosed connection embodiment for the oxygenator. It is also with the scope of the present invention to adapt any disclosed reservoir connection for use on the oxygenator, and vice versa.

The vertical mounting plate 124 of the carrier 82 includes a handle 94 and flanges 126 adapted to be slidingly engaged by the slotted track 133 on the mounting bracket 92. To attach the carrier 82 to the mounting bracket 92, the carrier 82 is lifted by the handle 94, and the flanges 126 are guided into the slotted track 133. In the illustrated embodiment, the slotted track 133 includes a retention pin 142 to secure the carrier 82 in the track 133 and prevent the carrier from descending too far into the mounting bracket 92. In an alternative preferred embodiment, the track may be tapered preferably so that it is narrower at the bottom than at the top, such as when used to receive tapered flanges 126'. Retention pins 142 may also be utilized with the tapered track and flanges.

Figure 8A:
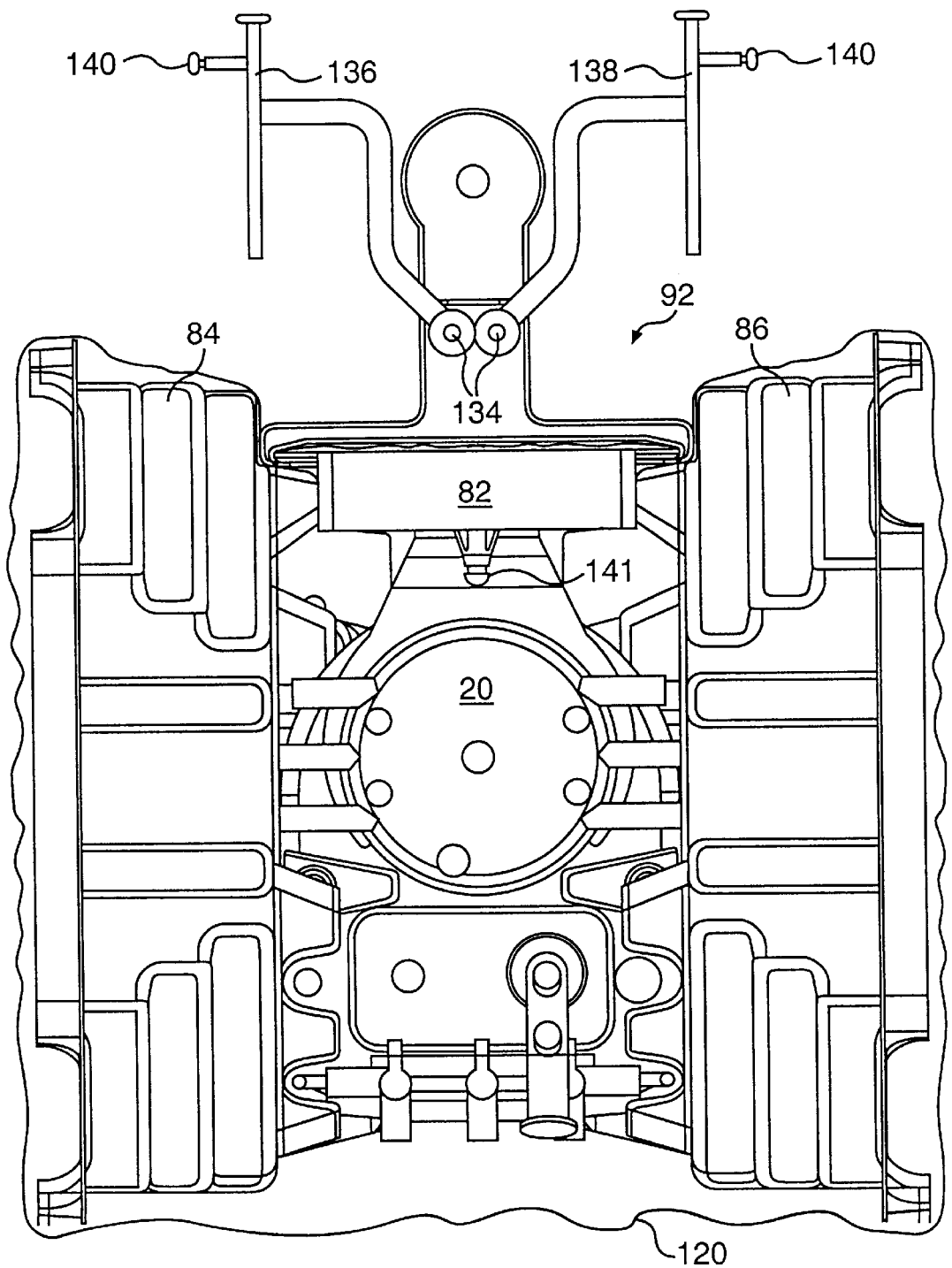
FIG. 8A is a top view of a preferred embodiment of the assembly pack of the present invention.
Figure 8B:
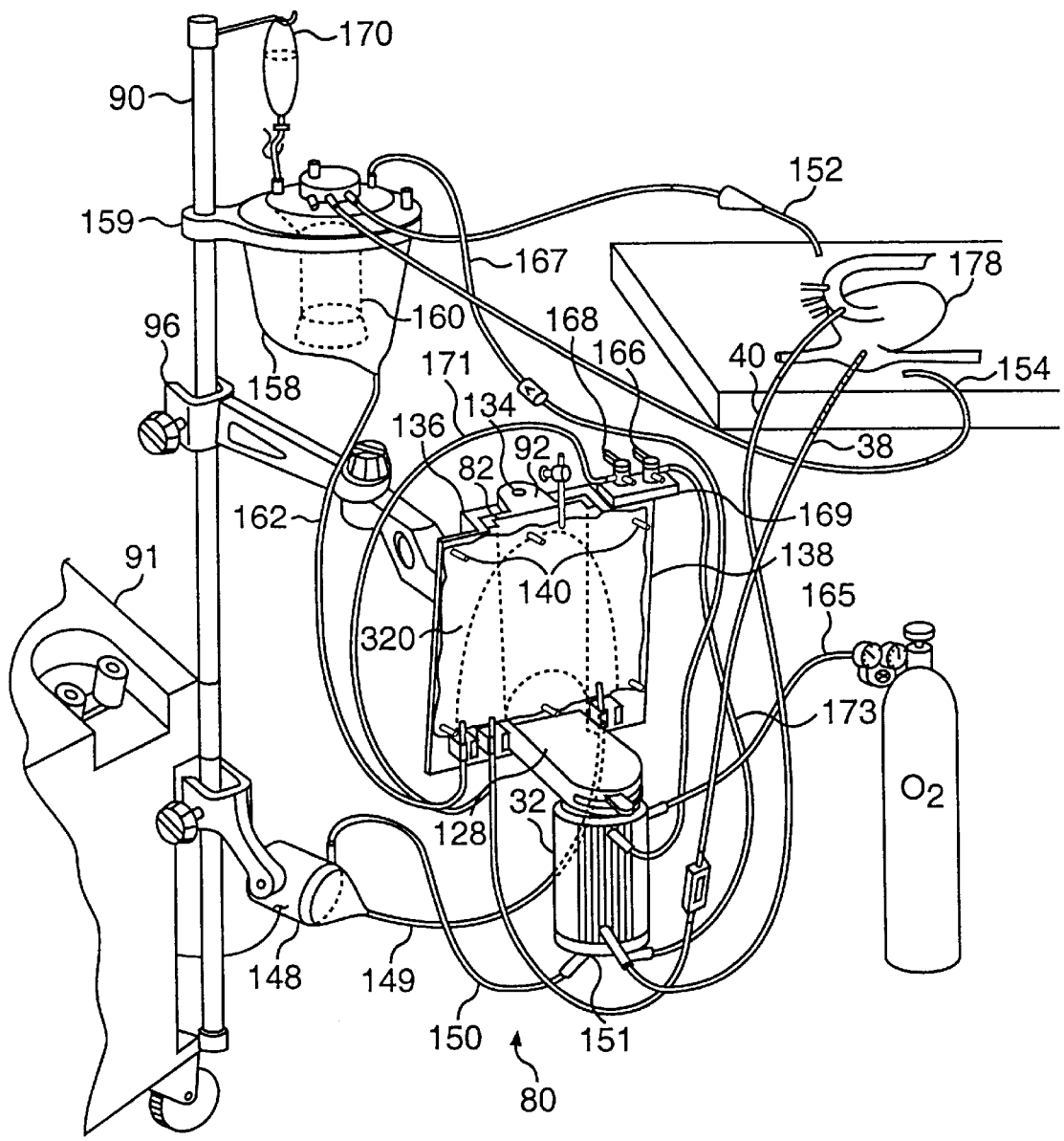
FIG. 8B is a perspective view of a further preferred embodiment of the assembly pack of the invention in a deployed configuration.

Referring to FIGS. 6A and 8A, in an alternative embodiment useful for mounting soft reservoir bags, the mounting bracket 92 includes two panels 136, 138 pivotally mounted on one or more hinges 134. The panels 136, 138 include pegs or clamps 140 for securing a soft reservoir bag in place, and may be pivoted into a position in which they overlay and are in a common plane with the front surface of the carrier 82. In this position the panels 136, 138 may securely suspend a reservoir bag for use. Further, the carrier 82 may be provided with one or more pegs 141 (as shown best in FIG. 7A) which assist in securing a soft reservoir bag in place during storage, pre-attachment, and once the panels are pivoted to their operative position. FIG. 8B shows a reservoir bag 320 attached to the embodiment of pivoting panels 136, 138 shown in FIG. 6A. The pegs 141 thus contribute to the correct locating of the bag 320 during product construction, shipping and storage prior to use. In addition to hardware for securing a reservoir bag, the panels 136, 138 may also be fitted with an apparatus for controlling the volume of blood in a reservoir bag, such as the apparatus described in commonly assigned U.S. application Ser. No. 09/079,046, the entire contents of which is incorporated herein by reference. The hinge 134 may optionally include only one pivotally mounted door and may be oriented horizontally or vertically.

When a soft reservoir bag is used, the pack assembly 80 may also include a hard shelled cardiotomy reservoir. In the undeployed configuration of this embodiment, the cardiotomy reservoir is secured on top of attachment plate 128 and the soft reservoir bag is preferably folded and retained on pins 141 between the cardiotomy reservoir and the vertical mounting plate 124.

FIG. 8B shows an embodiment of the pack assembly 80 with a soft reservoir 320 and a separate cardiotomy reservoir 158 deployed for use as part of an extracorporeal support circuit. In preparation of the pack assembly 80 for use in a surgical procedure, the components are positioned where necessary in the operating room. The carrier 82 with attached reservoir 320 and oxygenator 32 is attached to the mounting bracket 92. In this embodiment, the mounting bracket includes hinge(s) 134 and panels 136 and 138 with pegs or clamps for securing the soft reservoir bag 320. The mounting bracket 92 is attached by clamp 96 to mast 90 of the heart-lung machine 91 at a selected height. The cardiotomy reservoir 158 is removed from the top surface of the attachment plate 128 and elevated to a position above the blood reservoir by a hoop clamp 159 attached to the mast 90. Alternatively, the cardiotomy reservoir may be provided with a through hole 161 (shown in FIG. 7A) for receiving a mounting rod. Still further, a mechanism may be provided for telescoping the cardiotomy reservoir upwards to expose the venous reservoir therebehind, or the venous reservoir may be moved to a position which is lower than the cardiotomy reservoir rather than moving the cardiotomy reservoir. In such a closed system, it is important to note however that the drain from the venous blood reservoir 320 should be at a higher elevated position than the hollow fibers of the oxygenator in order to prevent possible negative pressure and subsequent entry of air into the oxygenator blood path that may then be delivered to the patient.

In use, the extracorporeal circuit of FIG. 8B is primed with saline solution from prime bag 170 before beginning the bypass procedure. After priming, deoxygenated blood is carried from the heart 178 to blood reservoir 320 by venous line 38. The venous blood is then drained from the reservoir 320 by line 149 and delivered by centrifugal pump 148 through line 150 to the oxygenator inlet port 151, where it is oxygenated and returned to the aorta by arterial line 40. Sucker lines 152, 154 collect cardiotomy blood from the incision site and deliver it to the cardiotomy reservoir 158. The cardiotomy blood is passed through a cardiotomy filter 160 and drained by cardiotomy outlet line 162 to the blood reservoir 320 where it is pooled with the venous blood for oxygenation with oxygen delivered by oxygen line 165. Excess air from the oxygenator 32 is vented by vent line 167 to the cardiotomy reservoir 158. A sampling manifold 169 is provided on the carrier 82 for monitoring the quality of blood in the system. Line 173 delivers oxygenated blood to arterial sampling port 166, and line 171 delivers venous blood to venous sampling port 168, for sampling and analysis.

Figure 9:
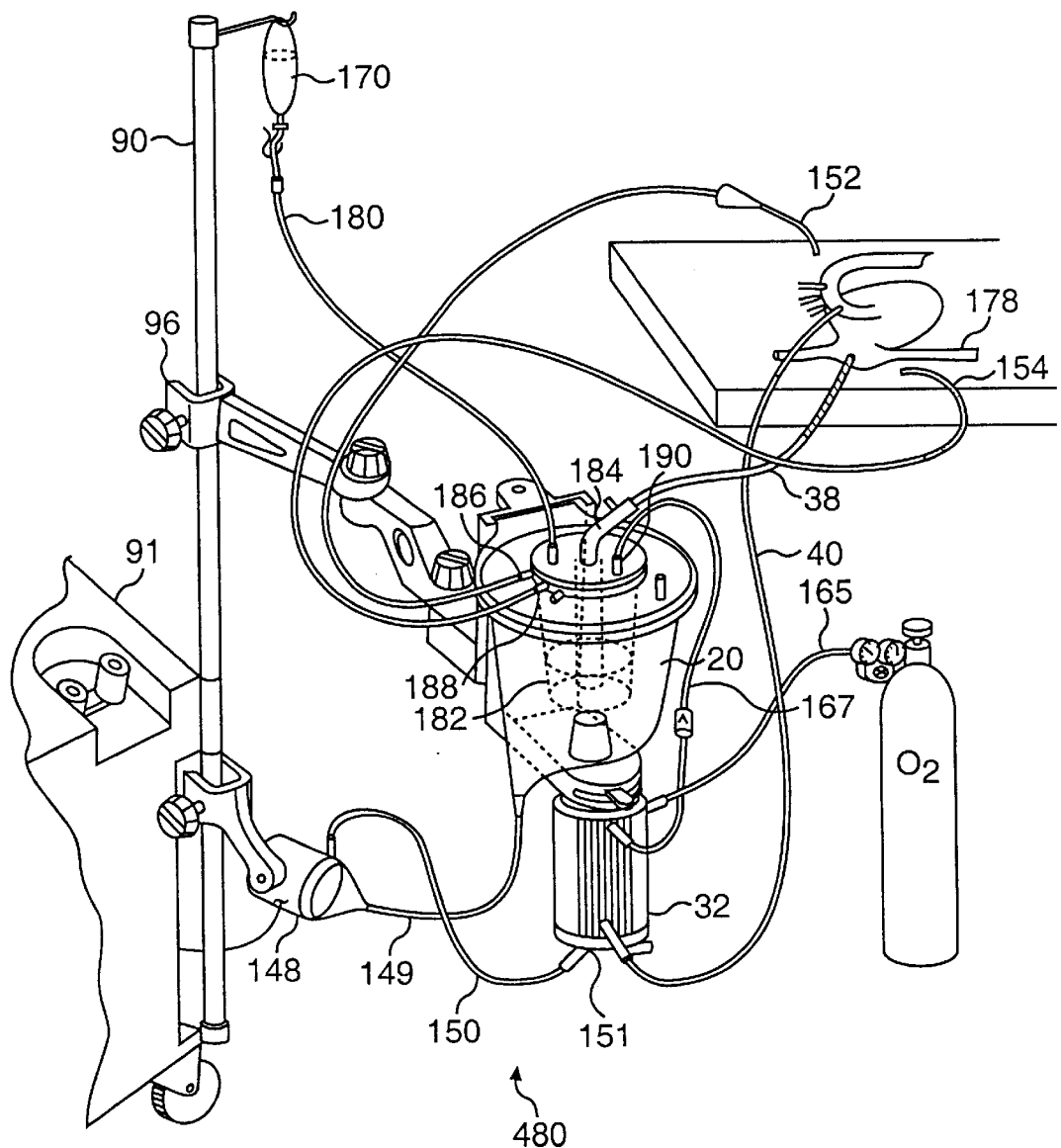
FIG. 9 is a perspective view of an alternative preferred embodiment of the assembly pack of the present invention in a deployed configuration.

FIG. 9 shows an alternative embodiment of the pack assembly 480 deployed for use as part of an extracorporeal support circuit. In this embodiment, a single hardshelled reservoir 20 is used that combines the venous reservoir and cardiotomy filter functions in one unit. The pack assembly 80 is deployed for use substantially as described above, except that a separate cardiotomy reservoir is not required and the mounting bracket 92 preferably does not include hinge 134 or doors 136 and 138. In use, the extracorporeal circuit is primed with saline solution delivered from prime bag 170 to the blood reservoir 20 by priming line 180. Deoxygenated venous blood is delivered to reservoir inlet port 184 by venous line 38 and pooled in the reservoir 20. The venous blood is then drained by line 149 and pumped by centrifugal pump 148 through line 150 to the oxygenator 32, where it is oxygenated by oxygen supplied through line 165. The oxygenated blood is then returned to the aorta through arterial line 40. Cardiotomy blood scavenged by suckers 152, 154 is delivered to cardiotomy ports 186, 188 and passed through cardiotomy filter 182 before being pooled with venous blood for oxygenation. Recirculation line 167 vents gas from the oxygenator 32 to port 190 on the blood reservoir 20.

Figure 10:
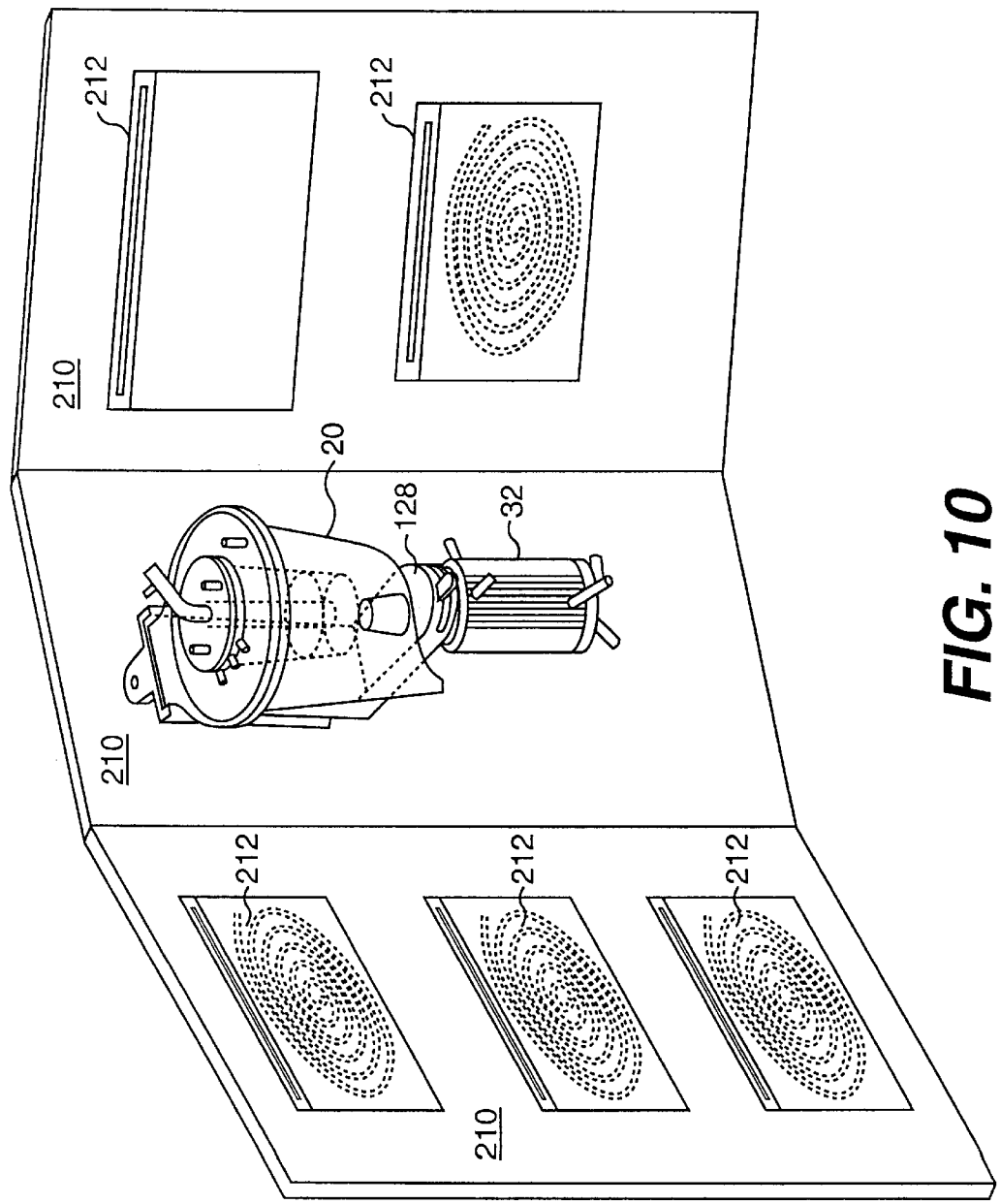
FIG. 10 is a perspective view of an alternative embodiment of the assembly pack of the present invention.

Referring to FIG. 10, a further embodiment of the present invention is shown in which the carrier and removable trays are replaced with folding support structures 210. A center support structure 210 can accommodate the reservoir 20 and/or the oxygenator 32, which are preferably connected by attachment plate 128. The center support structure 210 preferably includes a means for attaching the same to a mounting bracket or other structure for the desired end use. Each of the side support structures 210 can accommodate the various tubing groupings and other components required for the extracorporeal circuit in one of a plurality of side pockets or enclosures 212. The side support structures 210 are preferably transparent blister packs which sealingly enclose the contents in a sterile manner. The side support structures 210 are preferably removably connected to the center support structure through the use of side zippers or any other type of conventional flexible sealing mechanism. Thus, the side support structures 210 may fold inward to form a compact assembly for shipping and transport.

As should be apparent to one skilled in the art, the pack assembly 80 may provide convenient pre-made tubing connections and/or tubing packing arrangements for use in either a closed system or an open system, depending upon the customer's preference. This degree of versatility has heretofore never existed; all prior systems of been dedicated to either an open system or a closed system.

The present invention has now been described with reference to several embodiments thereof. The foregoing detailed description has been given for clarity and understanding only. No unnecessary limitations are to be understood therefrom. It will be apparent to those skilled in the art that many changes can be made in the embodiments described without departing from the scope of the invention. Thus, the scope of the present invention should not be limited to the exact details and structures described herein, but rather by the structures described by the language of the claims, and the equivalents of those structures.

What is claimed is:

1. A pack assembly for use in an extracorporeal blood circuit, comprising:
   (a) a carrier adapted to mount at least one blood handling apparatus;
   (b) at least one blood handling apparatus releasably attached to the carrier, said blood handling apparatus comprising at least one of a blood reservoir and a blood oxygenator;

wherein said carrier includes a handle mechanism for grasping by a user during lifting and repositioning of the pack assembly.

2. A pack assembly according to claim 1, further comprising:
at least one tray releasably attached to at least one of the carrier and the blood handling apparatus.

3. A pack assembly according to claim 2, wherein said at least one tray includes at least one partition for subdividing an interior area of said at least one tray into at least two sections.

4. A pack assembly according to claim 3, further comprising a cover extending over said at least one tray.

5. A pack assembly according to claim 4, wherein said cover is removably disposed so as to uncover only one of the at least two sections.

6. A pack assembly according to claim 3, wherein said at least one tray includes a plurality of partition guides and said at least one partition is removably disposed within one of said plurality of partition guides.

7. A pack assembly according to claim 1, further comprising:
a mounting bracket releasably engaged with the carrier.

8. A pack assembly according to claim 7, wherein said carrier includes mounting flanges and said mounting bracket includes a receiving channel for receiving said mounting flanges therein.

9. A pack assembly according to claim 8, further comprising:
a barrier pouch enclosing the carrier and the at least one blood handling apparatus, said barrier pouch being deformable so as to allow the engagement of said mounting flanges in said receiving channel of said mounting bracket without tearing said barrier pouch.

10. A pack assembly according to claim 9, wherein said barrier pouch includes means for removal from said pack assembly.

11. A pack assembly according to claim 8, wherein said mounting flanges include tapered edges and said mounting bracket includes a correspondingly tapered said receiving channel.

12. A pack assembly according to claim 2, wherein said at least one blood handling apparatus comprises two blood handling apparatuses, said two blood handling apparatuses including said blood reservoir and said blood oxygenator.

13. A pack assembly according to claim 12, further comprising a retainer bar for retaining said blood reservoir and said blood oxygenator in a mounted position.

14. A pack assembly according to claim 13, wherein said retainer bar is releasably engaged with said carrier.

15. A pack assembly according to claim 14, wherein said retainer bar includes at least one outwardly projecting tab for releasing said retainer bar from said carrier.

16. A pack assembly according to claim 12, further comprising a stabilizer clip for securing said blood reservoir.

17. A pack assembly for use in an extracorporeal blood circuit, comprising:
(a) a first support structure adapted to mount at least one blood handling apparatus;
(b) at least one blood handling apparatus releasably attached to said first support structure, said blood handling apparatus comprising at least one of a blood reservoir and a blood oxygenator; and
(c) at least one second support structure including an enclosure for sealingly enclosing at least one tubing line prior to use.

18. The pack assembly according to claim 17, wherein said at least one second support structure includes a tray and a cover disposed over an opening of the tray.

19. The pack assembly according to claim 18, wherein said cover defines a plurality of separately openable compartments within the tray.

20. The pack assembly according to claim 17, wherein said at least one second support structure is movable relative to said first support structure so as to fold inward.

21. A pack assembly for use in an extracorporeal blood circuit, comprising:
(a) a carrier adapted to mount a blood reservoir and a blood oxygenator, comprising:
(i) an attachment plate; and
(ii) a carrier base including a mounting plate, the mounting plate being adapted for mounting the carrier on a vertical support;
(b) a blood reservoir releasably attached to the attachment plate; and
(c) a blood oxygenator releasably attached to the attachment plate;
wherein said carrier includes a handle mechanism for grasping by a user during lifting and repositioning of the pack assembly.

22. The pack assembly according to claim 21, wherein said attachment plate includes upper and lower receiving channels, said blood reservoir and said blood oxygenator being slidingly received in a respective said receiving channel on the attachment plate.

23. The pack assembly according to claim 22, wherein said blood reservoir includes an adapter for cooperating with the respective receiving channel of the attachment plate.

24. The pack assembly according to claim 21, wherein said attachment plate includes an upper cylindrical boss for receiving said blood reservoir and a lower cylindrical socket for receiving said blood oxygenator.

25. The pack assembly according to claim 21, further comprising at least one removable tray.

* * * * *